US012690779B2

(12) United States Patent
Swanson et al.

(10) Patent No.: US 12,690,779 B2
(45) Date of Patent: Jul. 28, 2026

(54) METHODS FOR MAGNETIC RESONANCE IMAGING OF NANOCONSTRUCTS AND USES THEREOF

(71) Applicants:REGENTS OF THE UNIVERSITY OF MICHIGAN, Ann Arbor, MI (US); Kuva Labs Inc., Houston, TX (US)

(72) Inventors: Scott D. Swanson, Ann Arbor, MI (US); Thomas Hopkins, Sylvania, OH (US); Andrew Hopkins, Ann Arbor, MI (US)

(73) Assignees: REGENTS OF THE UNIVERSITY OF MICHIGAN, Ann Arbor, MI (US); Kuva Labs Inc., Houston, TX (US)

( * ) Notice: Subject to any disclaimer, the term of this patent is extended or adjusted under 35 U.S.C. 154(b) by 77 days.

(21) Appl. No.: 18/749,012

(22) Filed: Jun. 20, 2024

(65) Prior Publication Data
US 2025/0000384 A1     Jan. 2, 2025

Related U.S. Application Data

(60) Provisional application No. 63/522,007, filed on Jun. 20, 2023.

(51) Int. Cl.
| | |
|---|---|
| *A61B 5/055* | (2006.01) |
| *A61B 5/00* | (2006.01) |
| *A61K 41/00* | (2020.01) |
| *A61K 45/06* | (2006.01) |
| *A61K 49/12* | (2006.01) |
| *A61K 49/14* | (2006.01) |
| *G01R 33/50* | (2006.01) |

(Continued)

(52) U.S. Cl.
CPC ............ *A61B 5/055* (2013.01); *A61B 5/0044* (2013.01); *A61K 41/0071* (2013.01); *A61K 45/06* (2013.01); *A61K 49/126* (2013.01); *A61K 49/14* (2013.01); *G01R 33/50* (2013.01); *G01R 33/5618* (2013.01); *G01R 33/56341* (2013.01)

(58) Field of Classification Search
CPC .. A61B 5/055; A61B 5/0044; A61K 41/0071; A61K 45/06; A61K 49/126; A61K 49/14; G01R 33/50; G01R 33/5618; G01R 33/56341
See application file for complete search history.

(56) References Cited

U.S. PATENT DOCUMENTS

| | | | |
|---|---|---|---|
| 9,249,184 B2 | 2/2016 | Robbins et al. | |
| 11,406,721 B2 * | 8/2022 | Tsien ..................... | A61K 49/10 |

(Continued)

FOREIGN PATENT DOCUMENTS

WO     WO-2019/226785 A1     11/2019

OTHER PUBLICATIONS

Le Bihan, Molecular diffusion, tissue microdynamics and microstructure, NMR Biomed., 8(7-8):375-86 (1995).

(Continued)

*Primary Examiner* — Dixomara Vargas
(74) *Attorney, Agent, or Firm* — MARSHALL, GERSTEIN & BORUN LLP

(57)     ABSTRACT
Methods for imaging magnetic resonance imaging (MRI) agents containing nanoconstructs therein using diffusion-weighted fast-spin echo (FSE) or gradient-and-spin echo (GRASE) processes are described herein.

20 Claims, 5 Drawing Sheets
Specification includes a Sequence Listing.

(51) Int. Cl.
   *G01R 33/561*     (2006.01)
   *G01R 33/563*     (2006.01)

(56) References Cited

U.S. PATENT DOCUMENTS

| | | | | |
|---|---|---|---|---|
| 2011/0044524 | A1* | 2/2011 | Wang | G01R 33/5601 |
| | | | | 382/131 |
| 2014/0050670 | A1* | 2/2014 | Iyer | A61P 35/00 |
| | | | | 435/375 |
| 2015/0231269 | A1* | 8/2015 | Kaittanis | A61K 49/1854 |
| | | | | 514/263.24 |
| 2016/0195526 | A1* | 7/2016 | Venkatesan | G01R 33/448 |
| | | | | 435/7.1 |
| 2018/0021265 | A1* | 1/2018 | Grimm | A61P 35/00 |
| | | | | 424/489 |
| 2020/0101176 | A1* | 4/2020 | Hopkins | A61B 5/055 |
| 2021/0085790 | A1 | 3/2021 | Hopkins et al. | |
| 2022/0338750 | A1* | 10/2022 | Allen | A61B 90/37 |

| | | | | |
|---|---|---|---|---|
| 2023/0346986 | A1* | 11/2023 | Basilion | A61K 41/0038 |
| 2025/0213719 | A1* | 7/2025 | Nallathamby | H01F 1/344 |
| 2025/0271530 | A1* | 8/2025 | Zhang | G01R 33/243 |

OTHER PUBLICATIONS

Chu et al., Gradient- and spin-echo (GRASE) MR imaging: a long-existing technology that may find wide applications in modern era, Quantitative Imaging in Medicine and Surgery, 9(9):1477-84 (2019).

International Application No. PCT/US2024/034773, International Search Report and Written Opinion, mailed Sep. 27, 2024.

Park et al., Highly accelerated submillimeter resolution 3D GRASE with controlled T2 blurring in T2-weighted functional MRI at 7 Tesla: A feasibility study, Magn Reson Med., 85(5):2490-506 (2021).

Prasloski et al., Rapid whole cerebrum myelin water imaging using a 3D GRASE sequence, Neuroimage, 63(1):533-9 (2012).

Rosenthal et al., Sonodynamic therapy—a review of the synergistic effects of drugs and ultrasound, Ultrason. Sonochem., 11(6):349-63 (2004).

\* cited by examiner

METHODS FOR MAGNETIC RESONANCE IMAGING OF NANOCONSTRUCTS AND USES THEREOF

CROSS-REFERENCE TO RELATED APPLICATION

This application claims the benefit of and priority to U.S. Provisional Application No. 63/522,007 filed Jun. 20, 2023, the entire content of which is incorporated herein by reference for all purposes in its entirety.

REFERENCE TO SEQUENCE LISTING

The present application contains a Sequence Listing which has been submitted electronically in XML format and is hereby incorporated by reference in its entirety. Said XML copy is provided as a file entitled "59138A_SeqListing.xml" created on Jun. 18, 2024, which is 41,987 bytes in size.

FIELD OF THE INVENTION

The invention is generally in the field of imaging of magnetic resonance imaging (MRI) agents using diffusion-weighted fast-spin echo (FSE) or gradient-and-spin echo (GRASE) processes.

BACKGROUND OF THE INVENTION

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well-known reconstruction techniques. To perform such a scan, it is necessary to elicit NMR signals from specific locations in the subject. This is accomplished by employing magnetic fields which have the same direction as the polarizing field BO, but which have a gradient along the respective x, y and z axes. By controlling the strength of these gradients during each NMR cycle, the spatial distribution of spin frequencies can be controlled and the location of the resulting NMR signals can be identified. Scan time, however, is an important consideration in imaging, since reduced scan time increases patient throughput, improves patient comfort, and improves image quality by reducing motion artifacts. To this end, various techniques have been developed for acquiring NMR image data in a short time period.

One such technique is called "fast spin-echo" (FSE), which employs a pulse sequence for acquiring multiple k-space lines with one excitation. FSE is, for instance, much less sensitive to field inhomogeneities and gradient timing errors than, for example, echo planar imaging. Further, because the readout gradient is always positive, unlike echo planar imaging, gradient fidelity is less of a problem. Diffusion weighted FSE imaging employs gradient pulses at the beginning of the pulse sequence to sensitize the acquired NMR signals to spin motion. Conventional and diffusion weighted spin-echo imaging techniques are known in the art. Clinical diffusion-weighted imaging relies largely on the commercialization of single-shot echo-planar imaging (EPI) which, in turn, requires high-performance gradient coils to reduce artifacts related to off-resonance to diagnostically acceptable level. See Le Bihan D. Molecular diffusion, tissue microdynamics and microstructure. NMR Biomed. 1995; 8(7-8):375-86.

Another such technique is gradient-and-spin echo (GRASE), which employs and integrates aspects of EPI in FSE. GRASE can allow for collection of multiple gradient echoes within a fast spin echo (FSE) echo train. GRASE employs multiple refocusing radiofrequency (RF) pulses after the excitation RF pulse, similar to the fast spin-echo (FSE), but with series of gradient-echo readouts, which is similar to EPI inserted in the echo spacing interval between successive refocusing pulses. Each gradient-echo is preceded by appropriate phase encoding gradients to be filled in the k-space at corresponding locations to form an image. See, Chu, et al., "Gradient- and spin-echo (GRASE) MR imaging: a long-existing technology that may find wide applications in modern era", Quant Imaging Med Surg. 9(9): 1477-1484 (September 2019); Bihan D. Molecular diffusion, tissue microdynamics and microstructure. NMR Biomed. 1995; 8(7-8):375-86; Park S, et al., Highly accelerated submillimeter resolution 3D GRASE with controlled T2 blurring in T2-weighted functional MRI at 7 Tesla: A feasibility study. Magn Reson Med. 2021 May; 85(5):2490-2506; and Prasloski T, et al., Rapid whole cerebrum myelin water imaging using a 3D GRASE sequence. Neuroimage. 2012 Oct. 15; 63(1):533-9.

There is a need for developing improved methods of imaging agents using such techniques.

SUMMARY OF THE INVENTION

Methods of imaging magnetic resonance imaging (MRI) agents using diffusion-weighted fast-spin echo (FSE) or gradient-and-spin echo (GRASE) processes are described herein.

In various examples, the present invention provides improved methods of imaging different agents of interest using techniques, such as FSE and GRASE.

In further examples, the present invention provides methods of determining the concentration of different agents in vivo.

In yet further examples, the present invention provides improved methods for visualizing aspects of a tumor in a subject.

In one non-limiting instance, provided is a method of imaging a magnetic resonance imaging (MRI) agent, wherein the method includes the steps of:

(a) administering the MRI agent to a subject,
  wherein the MRI agent comprises nanoconstructs (NC) each having a plurality of equivalent protons and an average molecular weight in a range of about 300 Da to about 300 kDa and the nanoconstructs each have a T2 relaxation time greater than at least about 250 ms;

(b) using an MRI device to obtain a diffusion-weighted fast-spin echo (FSE) nuclear magnetic resonance scan of the nanoconstructs, wherein step (b) comprises:
  (i) applying diffusion filtering in range of about 500 to about 10,000 $s/mm^2$ to suppress water signals from the scan and selectively imaging the nanoconstructs;
  (ii) applying a signal acquisition bandwidth ranging from at least about 2 kHz to about 50 KHz; and
  (iii) obtaining greater than 8 spin echoes, optionally between 9 and 256 or between 9 and 128 spin echoes; optionally wherein step (b) further comprises modifying gain of a receiver-amplifier of the MRI device.

In another non-limiting instance, provided is a method of imaging a magnetic resonance imaging (MRI) agent, wherein the method involves a GRASE process, and includes the steps of:

(a') administering the MRI agent to a subject,
  wherein the MRI agent comprises nanoconstructs each having a plurality of equivalent protons and an average molecular weight in a range of about 300 Da to about 300 kDa and the nanoconstructs each have a T2 relaxation time greater than at least about 250 ms;

(b') using an MRI device to obtain a gradient-and-spin echo (GRASE) nuclear magnetic resonance scan of the nanoconstructs, wherein step (b') comprises:
  (i') applying diffusion filtering in range of about 500 to about 10,000 s/mm² to suppress water signals from the scan and selectively imaging the nanoconstructs;
  (ii') applying a signal acquisition bandwidth ranging from at least about 2 kHz to about 200 KHz; and
  (iii') obtaining greater than 8 spin echoes, optionally between 9 and 1024 spin echoes; and obtaining at least 3 gradient echoes, optionally between 3 and 7 gradient echoes;

optionally wherein step (b') further comprises modifying gain of a receiver-amplifier of the MRI device.

In some instances of the methods described herein, the NMR device is operated and the settings and/or parameters are selected to provide sufficient water and fat suppression to selectively image the MRI agent and nanoconstructs while suppressing all or substantially all of the water and/or fat signals, where "substantially all" refers to at least about 95%, 96%, 97%, 98%, or 99% or greater of the water and fat signals being suppressed from the scan(s). For example, a diffusion-based MRI imaging method can be employed where at least about 95% or greater of the signals associated with tissue and water are suppressed or eliminated (i.e., 100% absent or otherwise undetectable). The residual water can be removed by other water suppression methods known to those of skill in the art in imaging techniques. For example, to have additional water suppression, spectroscopic imaging where each voxel consists of an NMR spectrum with water, PEG, and fat can be used.

In instances of the above methods, the selection of particular imaging and/or diffusion parameters of the diffusion-weighted FSE and GRASE can be used to selectively detect the MRI agent and nanoconstructs. The signals for the MRI agent and nanoconstructs are proportional to their concentration.

The nanoconstructs include a backbone or platform which may have one or more additives associated thereto, and the NC acts an imaging agent. Such additives, as may be present on the nanoconstruct, can provide other capabilities, such as, for example, targeting to select a specific cell type, specific biological tissue or structure, or have specific membrane related properties, such as cellular membrane permeabilities.

The nanoconstructs each include a plurality of equivalent protons or substantially equivalent protons. In some instances, the plurality of equivalent or substantially equivalent protons ranges from about 30 to 27,000 protons, 200 to about 15,000 protons, or about 200 to about 10,000 protons, as well as any sub-ranges or individual values disclosed within. In some instances, the plurality of equivalent protons or substantially equivalent protons are selected from methylene protons, methyl protons, and/or methoxy protons.

In some instances, the nanoconstructs each have a T2 relaxation time greater than at least about 250 ms, 300 ms, 350 ms, 400 ms, 450 ms, or 500 ms. In some instances, the T2 relaxation time is at least about 250 ms to about 900 ms or about 500 ms to about 900 ms, as well as any sub-ranges or individual values disclosed within.

In some instances, the nanoconstructs each have translational diffusion coefficient of less than about $2 \times 10^{-10}$ m² s⁻¹, less than about $3 \times 10^{-11}$ m² s⁻¹, less than about $3.5 \times 10^{-11}$ m² s⁻¹, less than about $4 \times 10^{-11}$ m² s⁻¹, less than about $4.5 \times 10^{-11}$ m² s⁻¹, or less than about $5 \times 10^{-11}$ m² s⁻¹, when measured at 25 or 35° C. In some other instances, the nanoconstructs each have translational diffusion coefficient which is in a range of about $2 \times 10^{-10}$ m² s⁻¹ to about $5 \times 10^{-11}$ m² s⁻¹ when measured at 25 or 35° C., or any sub-range or individual value disclosed within.

In the methods described herein, the nanoconstructs can have one or more additives associated thereto. These additives include active agents which may be selected from the group consisting of targeting agents, therapeutic agents, chemotherapeutic agents, radiotherapeutic agents, photosensitizer agents, sonosentizer agents, imaging agents, diagnostic agents, photoacoustic agents, theranostic agents, and combinations thereof.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION OF THE INVENTION

Figure 1A:
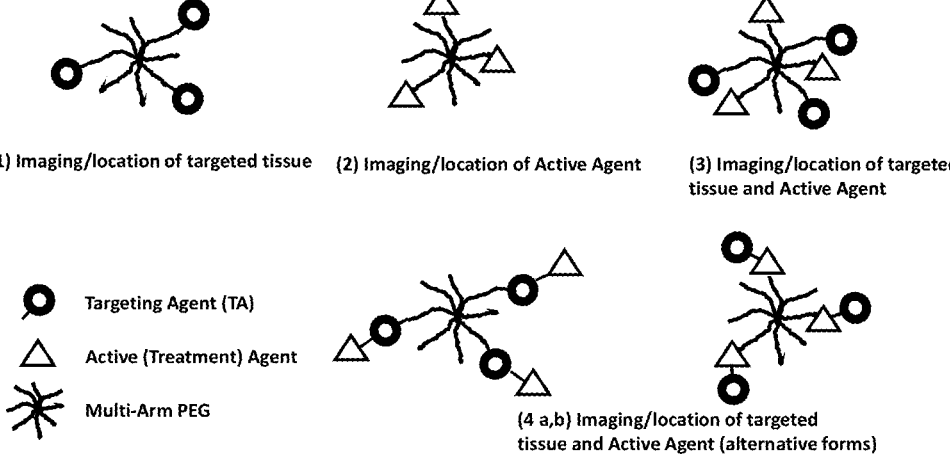
FIG. 1A is a non-limiting formulaic representation of a nanoconstruct (NC) having multiple arms (i.e., 8-armed PEG) with one or more additives associated thereon. Form (1) depicts a targeting agent (TA) conjugated or associated with the multi-arm PEG. Form (2) depicts an active agent, such as a therapeutic molecule, conjugated or associated with the multi-arm PEG. Forms (3) and (4a,b) depict alternative structures of the NC with both the TA and active agent conjugated or associated with the multi-arm PEG. These representations are not intended to be limiting in the amount or ratio of agents thereon.

Methods of imaging magnetic resonance imaging (MRI) agents using diffusion-weighted fast-spin echo (FSE) or gradient-and-spin echo (GRASE) processes are described below.

I. Definitions

The terms "nanoparticle" and "nanoconstruct", are used interchangeably to refer to particles having a volumetric shape that has at least one dimension which may range in size from about 1 nm to about 100 nm. In some instances, these volumetric shapes may have their largest cross-section from about 1 nm to about 100 nm. Such particles have a backbone material (e.g., a cage, support, matrix, or polymeric material) to which one or more additives, e.g., agents, moieties, compositions, biologics, and molecules, can be optionally associated to the backbone. The backbone material itself can be a nanoparticle.

The term "additive" refers to an active material having targeting, therapeutic, imaging, diagnostic, theranostic, or other capabilities, and combinations and variations of these.

The term "theranostic", refers to any suitable, agent, or material that has multiple capabilities and functions, including both imaging and therapeutic capabilities, both diagnostic and therapeutic capabilities, and combinations and variations of these and other features, such as targeting.

The terms "imaging", "imaging agent", "imaging apparatus or device" and similar such terms, generally include apparatus, agents, and materials that are able to enhance, provide, or enable the ability to detect, analyze and visualize the size, shape, position, composition, and combinations and variations of these as well as other features, of a structure, and in particular structures in animals, mammals, and humans. Imaging agents include contrast agents, dyes, and similar types of materials known in the field of imaging. Examples of an imaging apparatus or device include those used in various imaging methodologies including: x-ray imaging; magnetic resonance imaging; computer axial tomography (CAT); positron emission tomography (PET); ultrasound imaging; florescence imaging; and photo acoustic imaging.

The term "diagnostic", generally refers to identifying, determining, defining, and combinations and variations of these, conditions, diseases, or both, including conditions and diseases of animals, mammals and humans.

The terms "therapeutic" and "therapy" refer to addressing, treating, managing, mitigating, curing, preventing, and combinations and variations of these, conditions and diseases, including conditions and disease of animals, mammals and humans.

As used herein, unless stated otherwise, room temperature is at or about 25° C. Standard ambient temperature and pressure is 25° C. and 1 atmosphere. Unless expressly stated otherwise all tests, test results, physical properties, and values that are temperature dependent, pressure dependent, or both, are provided at standard ambient temperature and pressure, this also includes viscosities.

The term "subject" can refer to any animal. The animal may be a mammal, such as a human.

The term "spin echo," as used herein, refers to the application of a 1800 radio frequency (RF) pulse to refocus transverse magnetization that is dephasing due to magnetic field inhomogeneities as a function of time. In standard spin-echo imaging, a single 1800 RF pulse is used for each line of k-space. For fast spin echo imaging (FSE) a train of multiple 1800 RF pulses are used to acquire a desired number of k-space lines.

The term "gradient echo," as used herein, refers to the application of magnetic field gradients to sufficiently dephase and rephase transverse magnetization. A gradient echo is created by applying a prephasing gradient to position the transverse magnetization at the edge of k-space and is followed by a rephasing gradient. The gradient echo is created as the transverse magnetization crosses k=0; the point where all spatial components of transverse magnetization are in phase and signal is at a maximum. In conventional gradient echo imaging, a single gradient echo is acquired for each line of k-space. In other instances, such as gradient spin echo (GRASE), a number of gradient echoes may be acquired within a given spin echo. This is can typically be at least 3 gradient echoes for each spin echo, but may but may be up to 7 echoes.

Numerical ranges disclosed in the present application include, but are not limited to, ranges of relaxation times, ranges of bandwidths, ranges of integers, ranges of times, and ranges of echoes, etc. The disclosed ranges of any type, disclose individually each possible number that such a range could reasonably encompass, as well as any sub-ranges and combinations of sub-ranges encompassed therein. For example, disclosure of an integer range is intended to disclose individually every possible integer value that such a range could encompass, consistent with the disclosure herein.

Use of the term "about" is intended to describe values either above or below the stated value, which the term "about" modifies, in a range of approx. +/−10%; in other instances the values may range in value either above or below the stated value in a range of approx. +/−5%. When the term "about" is used before a range of numbers (i.e., about 1-5) or before a series of numbers (i.e., about 1, 2, 3, 4, etc.) it is intended to modify both ends of the range of numbers or each of the numbers in the series, unless specified otherwise.

II. Methods of Molecular Imaging a Magnetic Resonance Imaging (MRI) Agent

Methods of imaging magnetic resonance imaging (MRI) agents using diffusion-weighted fast-spin echo (FSE) or gradient-and-spin echo (GRASE) processes are described herein.

In one non-limiting instance, a method of imaging a magnetic resonance imaging (MRI) agent includes the steps of:

(a) administering the MRI agent to a subject,
    wherein the MRI agent comprises nanoconstructs each
        having a plurality of equivalent protons and an
        average molecular weight in a range of about 300 Da
        to about 300 kDa and the nanoconstructs each have
        a T2 relaxation time greater than at least about 250
        ms;
(b) using an MRI device to obtain a diffusion-weighted
    fast-spin echo (FSE) nuclear magnetic resonance scan
    of the nanoconstructs, wherein step (b) comprises:
    (i) applying diffusion filtering in range of about 500 to
        about 10,000 s/mm$^2$ to suppress water signals from
        the scan and selectively imaging the nanoconstructs;
    (ii) applying a signal acquisition bandwidth ranging
        from at least about 2 kHz to about 50 KHz; and
    (iii) obtaining greater than 8 spin echoes, optionally
        between 9 and 256 or between 9 and 128 spin
        echoes; optionally wherein step (b) further com-
        prises modifying gain of a receiver-amplifier of the
        MRI device.

In the above method, the translational diffusion coefficient of each nanoconstruct is typically less than about $2\times10^{-10}$ m$^2$ s$^{-1}$.

In some instances of the diffusion-weighted fast-spin echo (FSE) method above, one or more additives are associated to the nanoconstructs which include a targeting agent, such as a tumor targeting agent; and the method further comprises, following step (b):

(c) providing data identifying the shape, structure, and/or
        position of a tumor in the subject.

In some instances, the data in step (c) further includes data regarding the relative abundance of specific receptors or other genotype information relating to the tumor in the subject. For instance, the scanned MRI agent and the proton signal intensity produced from the imaging of the nanoconstructs can be used to target and extrapolate the relative abundance of a receptor, defining its genotype. Exemplary receptor targeting agents, which can be used to target a receptor, can include, but are not limited to: folate, iRGD, iNGR, PSMA, cRGD, gastrin-releasing peptide receptor (GRPR), human epidermal growth factor receptor 2 (HER2), insulin-like growth factor 1 receptor (IGF-1R), fibroblast growth factor receptor 3 (FGFR3), EGFR antibodies, P53, fucoidan, and combinations thereof. Other receptor targeting agents can include integrin binding targeting agents which represent a family of targets with heightened interest due to their reliable prevalence in tumors and connection to progression/prognosis.

In some instances of the diffusion-weighted fast-spin echo (FSE) method above, the method further includes:

(d), following step (b), providing data on the concentra-
        tion of the nanoconstructs in the subject.

In another non-limiting instance, a method of imaging a magnetic resonance imaging (MRI) agent, the method involves a GRASE process, the method includes the steps of:

(a') administering the MRI agent to a subject,
        wherein the MRI agent comprises nanoconstructs each
            having a plurality of equivalent protons and an
            average molecular weight in a range of about 300 Da
            to about 300 kDa and the nanoconstructs each have
            a T2 relaxation time greater than at least about 250
            ms;
    (b') using an MRI device to obtain a gradient-and-spin
        echo (GRASE) nuclear magnetic resonance scan of the
        nanoconstructs, wherein step (b') comprises:

(i') applying diffusion filtering in range of about 500 to
            about 10,000 s/mm2 to suppress water signals from
            the scan and selectively imaging the nanoconstructs;
        (ii') applying a signal acquisition bandwidth ranging
            from at least about 2 kHz to about 200 KHz; and
        (iii') obtaining greater than 8 spin echoes, optionally
            between 9 and 1024 spin echoes; and obtaining at
            least 3 gradient echoes, optionally between 3 and 7
            gradient echoes;
    optionally wherein step (b) further comprises modifying
    gain of a receiver-amplifier of the MRI device.

In the method immediately described above, the translational diffusion coefficient of each nanoconstruct is typically less than about $2\times10^{-10}$ m$^2$ s$^{-1}$.

In some instances of the GRASE method above, one or more additives are associated to the nanoconstructs which include a targeting agent, such as a tumor targeting agent; and the method further comprises, following step (b'):

(c') providing data identifying the shape, structure, and/or
        position of a tumor in the subject.

In some instances, the data in step (c') further includes data regarding the relative abundance of specific receptors or other genotype information relating to the tumor in the subject. For instance, the scanned MRI agent and the proton signal intensity produced from the imaging of the nanoconstructs can be used to target and extrapolate the relative abundance of a receptor, defining its genotype. Exemplary receptor targeting agents, which can be used to target a receptor, can include, but are not limited to: folate, iRGD, iNGR, PSMA, cRGD, gastrin-releasing peptide receptor (GRPR), human epidermal growth factor receptor 2 (HER2), insulin-like growth factor 1 receptor (IGF-1R), fibroblast growth factor receptor 3 (FGFR3), EGFR antibodies, P53, fucoidan, and combinations thereof. Other receptor targeting agents can include integrin binding targeting agents which represent a family of targets with heightened interest due to their reliable prevalence in tumors and connection to progression/prognosis.

In some instances of the GRASE method above, the method can further include:

(d'), following step (b'), providing data on the concentra-
        tion of the nanoconstructs in the subject.

In instances of the first method described above, diffusion-weighted FSE relies on the diffusion constant and transverse spin relaxation rate of the nanoconstructs of the MRI agent, where a slow diffusion constant and transverse spin relaxation rate combine to allow diffusion weighted MRI sequences which suppress surrounding water signals, providing a clear image of the MRI agent and nanoconstructs.

In some instances of the above methods, the NMR device is operated and the settings and/or parameters are selected to provide sufficient water and fat suppression to selectively image the MRI agent and nanoconstructs while suppressing all or substantially all of the water and/or fat signals, where substantially all refers to at least about 95%, 96%, 97%, 98%, or 99% or greater of the water and fat signals being suppressed from the scan(s). For example, a diffusion-based MRI imaging method can be employed where at least about 95% or greater of the signals associated with tissue and water are suppressed or eliminated (i.e., 100% absent or otherwise undetectable). The residual water can be removed by other water suppression methods known to those of skill in the art in imaging techniques. For example, to have additional water suppression, spectroscopic imaging where each voxel consists of an NMR spectrum with water, PEG, and fat can be used. In some instances, fat suppression or fat saturation techniques can be applied to remove any remnants of imaging due to fat, the NMR device used for the above methods may incorporate fat suppression techniques known to the skilled person. For instance, fat suppression techniques in magnetic resonance imaging (MRI) are techniques used to selectively suppress the signal from fat tissue in order to improve the visualization of structures or pathologies that may be obscured by the presence of fat. Without limitation, fat suppression techniques used in MRI can include: chemical fat saturation; inversion recovery (IR) with fat suppression; spectral fat saturation; saturation bands; and/or fat-water separation techniques. Advantageously, fat protons resonate at a chemical shift different from water and PEG, and can be effectively suppressed by a variety of methods and techniques, as described elsewhere above. Fat suppression is often done in MRI, especially body MRI, to provide a clearer picture of the diagnostic water proton image. One method of fat suppression applies an RF pulse on the at the fat frequency to suppress the signal arising from fat protons. These methods can be combined in vivo to create a fat-suppressed, PEG selective image.

In instances of the above methods, the selection of particular imaging and/or diffusion parameters of the diffusion-weighted FSE and GRASE can be used to selectively detect the MRI agent and nanoconstructs. The signals for the MRI agent and nanoconstructs are proportional to their concentration. In some instances, a combination of a high b value (such as of at least about 5000 s/mm2) and long TE time (such as of at least about 245 ms) effectively suppress the water signal but do not sufficiently suppress long-T2 fat signals, creating an image that is a superposition of PEG and fat signals. However, MRI images taken without such high b values and long TE times will show a conventional water proton image. In some cases, by adding such high b-values and long TE times in combination with fat suppression can sufficiently reduce both water and fat signal to create a PEG selective image.

In some instances, the methods may be used as theranostic methods. For example, when the methods described above are theranostic methods, a targeted theranostic nanoconstruct is delivered to the subject, and is carried by the blood and associates with a targeted structure, e.g., a tumor. A nuclear magnetic resonance scan of the tumor is taken in steps (b) or (b'), and the image produced is enhanced by the presence of the nanoconstructs of the MRI agent. The position and shape of the targeted structure in the body of the subject is obtained and stored. Subsequent image techniques, e.g., photo acoustic imaging, modeling techniques, e.g., computer enhancements and rendering of the initial MRI image, and combinations thereof can be used to provide very precise image and position data and information for the targeted structure in the body of the subject. An illumination pattern can then be developed based upon this image and position data. This illumination pattern can be predetermined, customized and specific to the targeted structure.

For the MRI agents described, these include a plurality of nanoconstructs therein. The MRI agents can be provided as pharmaceutical compositions, in kits, and in systems. Compositions containing the MRI agent can be in the form of pharmaceutical grade compositions or solutions. The compositions or solutions can be prepared in a suitable pharmaceutical grade solvent(s) and can include one or more known pharmaceutical excipients, as appropriate. They can also be in the form of pills or tablets, instead of liquid compositions. Such liquid or solid compositions include the MRI agents, including a plurality of nanoconstructs therein, at concentrations of about 1 mg/kg to 200 mg/kg of body weight, 10-100 mg/kg, or 20-50 mg/kg, and any sub-ranges or individual concentrations contained within the aforementioned ranges. Such MRI agents can be administered to a subject by any suitable means, including orally, transdermally, or intravenously (using an injection, a catheter, or other intravenous or intraarterial delivery methods).

The concentration of the nanoconstructs in an MRI agent, when provided as pharmaceutical compositions for administration to a subject, is not particularly limited. In some instances, the concentration of the nanoconstructs in a pharmaceutical composition can be, for example, about 10 wt % in saline, when administered at 25 mg/kg, equating to 1750 mg for a 70 kg individual. Additional inactive ingredients may be included in the composition(s), which can include without limitation: buffers (such as citrate, phosphate, carbonate buffers), preservatives, vitamins, surfactants, liposomal materials (e.g., DSPC), proteins (e.g. albumin, lactose), alcohols, sugars, anti-oxidants (e.g., butylated hydroxyanisole), anti-inflammatories, salts, cholesterol, or amino acids. Other excipients, such inactive or active additives known for pharmaceutical use may also be present.

A. Diffusion-Weighted FSE and GRASE Imaging Parameters

In instances of the first and second methods, the diffusion-weighted FSE and GRASE processes include the selection of several parameters, as discussed below.

For instance, the diffusion-weighted FSE methods include applying diffusion filtering in a range of about 500 to about 10,000 s/mm², or sub-ranges disclosed within, to suppress water signals from the scan and selectively imaging the nanoconstructs of the MRI agent. The FSE method further includes applying a signal acquisition bandwidth ranging from at least about 2 kHz to about 50 KHz or about 5 kHz to about 50 KHz, as well as sub-ranges and individual bandwidth values contained within. In some instances, the signal acquisition bandwidth is about 10 KHz. The FSE method further includes obtaining greater than 8 spin echoes, such as between 9 to 256 or between 9 to 128 spin echoes, as well as sub-ranges and individual echo values contained within. In some cases, at least 16, 32, 64, or 128 spin echoes are obtained during the method. In some instances, the FSE methods only obtain spin echoes and exclude obtaining any gradient echoes. In some instances, the FSE method optionally includes modifying the gain of a receiver-amplifier of the MRI device. For example, gain can be modified by increasing the receiver gain by between 6 dB and 50 dB of the MRI system to deliver an analog signature greater than 0.1 V and less than 1.0 V to the digitizer. With selective PEG imaging, the water signal is sufficiently attenuated, such that the water signal is attenuated to allow the detection of the PEG signal, so that the receiver gain may be increased to digitize the remaining PEG signal. Increasing receiver gain increased the sensitivity of selective PEG imaging.

In some instances, one or more imaging parameters of the nuclear magnetic resonance scan of the FSE methods can be selected from:

(i) repetition time (TR), which can be from between about 2 seconds to about 10 seconds, about 2 seconds to about 4 seconds, or about 3 seconds to about 5 seconds, as well as sub-ranges and individual values disclosed within;

(ii) spin echo time (TE), which can be from between about 50 ms to about 100 ms, as well as sub-ranges and individual values disclosed within the specified range;

(iii) gain, which can be from between about 6 to 50 dB, as well as sub-ranges and individual values disclosed within;

(iv) spectral width (sw), which can be from between about 2,000 to about 50,000 Hz, about 4,000 to about 10,000 Hz, as well as sub-ranges and individual values disclosed within; or, where in some instances the spectral width can be about 5,000 Hz;

(v) b value, which can be about from between about 500 to 10,000 s/mm$^2$, as well as sub-ranges and individual values disclosed within; or wherein the b value can be about 4,000 or 5,000 s/mm$^2$;

(vi) voxel size, which can be about 1.5 to about 15 microliters;

(vii) spin echo train length, which can range from 9 to 256 or between 9 and 128 spin echoes;

(viii) echo train segments, which can be from between 1 to 8 segments, as well as sub-ranges and individual values disclosed within; or, wherein the echo train segments is 1; and combinations of the above imaging parameters.

In some instances, one or more diffusion parameters of the nuclear magnetic resonance scan of the FSE methods can be selected from:

(ix) a delta value ranging from about 6 ms to about 40 ms, or sub-ranges or individual values contained within;

(x) diffusion gradient, which can be from between about 3 Gauss/cm to about 25 Gauss/cm, as well as sub-ranges and individual values disclosed within; or, wherein the diffusion gradient is about 12 Gauss/cm; and combinations of the above diffusion parameters.

Combinations of two or more of the above imaging and diffusion parameters may also be selected for performing the nuclear magnetic resonance scan during an FSE method described.

For the diffusion-weighted FSE methods, the nanoconstructs of the MRI agent include a plurality of equivalent or substantially equivalent protons which are directly detected and measured. This differs from MRI using metals, such as gadolinium, which changes the relaxation time of the water protons it interacts with, thereby creating a contrast that is visible during scanning. Thus, the FSE method provides images based upon the direct measurement of protons in the nanoconstructs of the MRI agent, and does not rely upon, and does not use, changes in the relaxation time of water protons.

The diffusion-weighted FSE methods described above can produce and detect a signal which is at least about 5, 10, 15, 20, 25, or 30 times greater than the signal detected using a conventional spin-echo technique scanning the same MRI agent. Further, the same methods permit nuclear magnetic resonance scans of the MRI agent to be taken when the nanoconstructs are at concentrations of as low as 0.05 mg/mL. The ability to suppress water signal and selectively image low concentrations of nanoconstructs by the claimed methods is not viable using other known nuclear magnetic resonance imaging techniques.

For the GRASE methods, the selection of the following parameters is relevant to the methods described. For instance, GRASE acquires several gradient echoes within each of many spin echoes. This is in contrast to FSE methods, such as those described above, which do not include gradient echoes. GRASE parameters that will be adjusted to include the number of gradient echoes, the number of data points per each echo, and the digitization rate to acquire each echo. In some instances, GRASE methods can include applying diffusion filtering in a range of about 500 to about 10,000 s/mm$^2$, or sub-ranges disclosed within, to suppress water signals from the scan and selectively imaging the nanoconstructs of the MRI agent. The GRASE method further includes applying a signal acquisition bandwidth ranging from at least about 2 kHz to about 200 KHz or about 5 kHz to about 100 KHz, as well as sub-ranges and individual bandwidth values contained within. The GRASE methods further include obtaining at least 3 gradient echoes, such as between 3 to 7 gradient echoes, as well as sub-ranges and individual echo values contained within. In some cases, at least 8 and potentially up to 1024 spin echoes are obtained during the GRASE method. The GRASE methods further include obtaining at least 3 gradient echoes, such as between 3 to 7 gradient echoes, as well as sub-ranges and individual echo values contained within. In some cases, at least 3 to 7 gradient echoes are obtained during the GRASE method. In some instances, the GRASE method optionally includes modifying the gain of a receiver-amplifier of the MRI device. For example, gain can be modified by increasing the receiver gain by between 6 dB and 50 dB of the MRI system to deliver an analog signature greater than 0.1 V and less than 1.0 V to the digitizer. With selective PEG imaging, the water signal is sufficiently attenuated, such that the water signal is attenuated to allow the detection of the PEG signal, so that the receiver gain may be increased to digitize the remaining PEG signal. Increasing receiver gain increased the sensitivity of selective PEG imaging.

In some instances, one or more imaging parameters of the nuclear magnetic resonance scan of the GRASE methods can be selected from:

(i) repetition time (TR), which can be from between about 2 seconds to about 10 seconds, about 2 seconds to about 4 seconds, or about 3 seconds to about 5 seconds, as well as sub-ranges and individual values disclosed within;

(ii) spin echo time (TE), which can be from between about 50 ms to about 100 ms, as well as sub-ranges and individual values disclosed within;

(iii) gain, which can be from between about 6 to 50 dB, as well as sub-ranges and individual values disclosed within the specified range;

(iv) spectral width (sw), which can be from between about 2,000 to about 50,000 Hz, about 4,000 to about 10,000 Hz, as well as sub-ranges and individual values disclosed within; or, where in some instances the spectral width can be about 5,000 Hz;

(v) b value, which can be about from between about 500 to 10,000 s/mm$^2$, as well as sub-ranges and individual values disclosed within; or wherein the b value can be about 4,000 or 5,000 s/mm$^2$;

(vi) voxel size, which can be about 1.5 to about 15 microliters;

(vii) spin echo train length, which can range from 9 to 1024 spin echoes;

(viii) gradient echo train length, which can range from 9 to 1024 gradient echoes;

(ix) echo train segments, which can be from between 1 to 8 segments, as well as sub-ranges and individual values disclosed within; or, wherein the echo train segments is 1; and combinations of the above imaging parameters.

In some instances, one or more diffusion parameters of the nuclear magnetic resonance scan of the GRASE methods can be selected from:

(x) a delta value ranging from about 6 ms to about 40 ms, or sub-ranges or individual values contained within;

(xi) diffusion gradient, which can be from between about 3 Gauss/cm to about 25 Gauss/cm, as well as sub-ranges and individual values disclosed within; or, wherein the diffusion gradient is about 12 Gauss/cm; and combinations of the above diffusion parameters.

Combinations of two or more of the above imaging and diffusion parameters may also be selected for performing the nuclear magnetic resonance scan during a GRASE method described.

Figure 3:
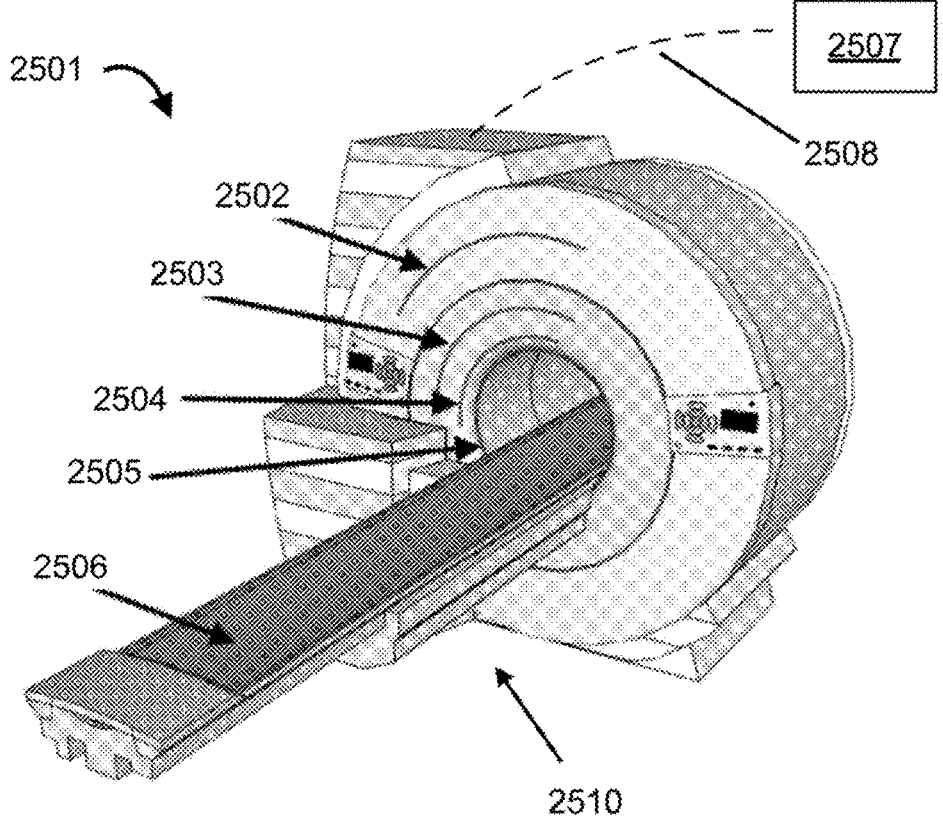
FIG. 3 shows a schematic diagram of an exemplary MRI system 2501. The exemplary system 2501 includes a magnet 2502, gradient coils 2503, radio frequency coils 2504, a bore 2505 and a table 2506.

The diffusion-weighted fast-spin echo (FSE) or GRASE nuclear magnetic resonance scans are applied using an MRI device. FIG. 3 shows a non-limiting schematic diagram of a non-limiting example of an MRI system 2501. The system 2501 has a magnet 2502, gradient coils 2503, radio frequency coils 2504, a bore 2505 and a table 2506. It being understood that FIG. 3 is a schematic representation, that other components and other configurations and types of MRI systems may be employed. The system 2501, in some cases, is configured to generate three magnetic fields. The first field is a strong static magnetic field to create energy level differences in nuclei with spin angular momentum and gives rise to bulk nuclear magnetization. The second field is a radio frequency field and is used to tip the created nuclear magnetization so that it can be detected by RF coils 2504. The third field is a set of magnetic field gradients is used to spatially encode the signal to create a map of nuclear magnetization. Thus, in some instances, the magnetic fields are configured to generate an image of non-water protons present in an additive placed in a subject to be imaged; wherein the magnetic field gradients can be pulsed in a specific manner to sensitize the nuclei to motion due to flow or diffusion.

In some instances of the methods described, the MRI agent made up of the nanoconstructs is administered to a subject (i.e., patient). The patient with the administered imaging agent is then placed on table 2506, the table is moved into the bore 2505, and the system 2501 performs a scan, obtains MRI images, of for example the types disclosed herein. The nanoconstructs are directly imaged providing a detailed image, and data, regarding their position in the patient.

In some instances, MRI system 2501 has a control system 2507, which includes operator input and other control features, as well as operating instruction, such as computer code. The control system 2507 is in control communication with the device 2510, as shown by dashed line 2508. By control communications it is meant that data, information and control commands as well as other instructions are communicated between the control system 2507 and the device 2510. The control system 2507 may be separate from the device 2510, or it may be a part of the device 2510, e.g., within the structure of the device 2510. In an embodiment, instructions to operate the MRI to provide the operating parameters for imaging PEG based nanoparticles are provided to the system 2501. This can be way of a software upgrade, for example. In this manner existing MRI systems can be readily upgraded to employ the benefits of the present methods for imaging MRI agents, as described.

B. Nanoconstructs

The nanoconstructs (NCs) include a backbone or platform which may have one or more additives associated thereto, and the NC acts an imaging agent. Additives, when present on the nanoconstruct, can provide other capabilities, such as, for example, targeting to select a specific cell type, specific biological tissue or structure, or have specific membrane related properties, such as cellular membrane permeabilities.

The NCs associated with the backbone or platform may be covalently or non-covalently attached to the backbone or platform.

In some instances, the nanoconstructs include a backbone or platform and do not have any additives associated thereto. In such instances, the NC alone is able to bioaccumulate in tissue(s) and act an imaging agent. The ability to bioaccumulate in tissue(s) is believed to be related to the molecular weight of the NC, where increasing molecular weight results in increased bioaccumulation in tissue(s).

The NCs described herein are nontoxic and biocompatible, and the NCs can act as a molecular imaging agent for use in various magnetic resonance imaging (MRI) techniques.

For the methods described, each of the nanoconstructs can have an average molecular weight in a range of about 300 Da to about 300 kDa, about 3 kDa to about 300 kDa, about 10 kDa to about 300 kDa, or about 3 kDa to about 200 kDa, as well as any sub-ranges or individual values disclosed within. In some instances, each of the nanoconstructs has an average molecular weight in a range of about 10 kDa to about 250 kDa, as well as any sub-ranges or individual values disclosed within. In certain instances, the nanoconstructs (NCs) do not include any additives associated thereto and bioaccumulate in tissue(s). Optionally, NCs contain a polymer that does not contain an additive associated therewith, and the NCs have a molecular weight of about 50 kDa to about 300 kDa, about 50 kDa to about 250 kDa, about 50 kDa to about 200 kDa, or about 100 kDa to about 200 kDa, as well as any sub-ranges or individual values disclosed within. Optionally, NCs contain multi-arm PEG and each of the arms of the PEG does not contain an additive associated therewith, and the NCs have a molecular weight of about 50 kDa to about 300 kDa, about 50 kDa to about 250 kDa, about 50 kDa to about 200 kDa, or about 100 kDa to about 200 kDa, as well as any sub-ranges or individual values disclosed within.

In some instances, the nanoconstructs of the MRI agent have an average hydrodynamic diameter of less than about 50 nm. In some instances, the nanoconstructs of the MRI agent may be selected to have an average hydrodynamic diameter of less than about 25 nm, less than about 15 nm or less than about 7 nm, or less. Sub-ranges or individual values disclosed for the above are possible. In some instances, the nanoconstructs have a size or dimension, defined as a cross section from about 5 nm to about 20 nm, from about 5 nm to about 15 nm, from about 10 nm to about 15 nm, and from about from about 9 nm to about 12 nm. A relatively small sized (i.e., <20 nm) nanoconstruct can allow for ease of penetration of a targeted tissue or structure, including, as an example, very dense tissue, such as muscle.

The nanoconstructs each include a plurality of equivalent protons or substantially equivalent protons. "Substantially equivalent protons," as used herein, refers to protons that would experience the same chemical shift due to molecular symmetry. In some instances, the plurality of equivalent or substantially equivalent protons ranges from about 30 to 27,000 protons, 30 to 25,000 protons, 30 to 20,000 protons, 30 to 15,000 protons, 30 to 10,000 protons, 200 to about 15,000 protons, or about 200 to about 10,000 protons, as well as any sub-ranges or individual values disclosed within. In some instances, the plurality of equivalent protons or substantially equivalent protons are selected from methylene protons, methyl protons, and/or methoxy protons.

In some instances, the nanoconstructs each have a T2 relaxation time greater than at least about 250 ms, 300 ms, 350 ms, 400 ms, 450 ms, or 500 ms. In some instances, the T2 relaxation time is at least about 250 ms to about 900 ms or about 500 ms to about 900 ms, as well as any sub-ranges or individual values disclosed within.

In some instances, the nanoconstructs each have translational diffusion coefficient of less than about $2\times10^{-10}$ m$^2$ s$^{-1}$, less than about $3\times10^{-11}$ m$^2$ s$^{-1}$, less than about $3.5\times10^{-11}$ m$^2$ s$^{-1}$, less than about $4\times10^{-11}$ m$^2$ s$^{-1}$, less than about $4.5\times10^{-11}$ m$^2$ s$^{-1}$, or less than about $5\times10^{-11}$ m$^2$ s$^{-1}$, when measured at 25 or 35° C. In some other instances, the nanoconstructs each have translational diffusion coefficient which is in a range of about $2\times10^{-10}$ m$^2$ s$^{-1}$ to about $5\times10^{-11}$ m$^2$ s$^{-1}$, when measured at 25 or 35° C., or any sub-range or individual value disclosed within.

Various additional aspects of the nanoconstructs are described below.

1. Backbone or Platform

Figure 1B:
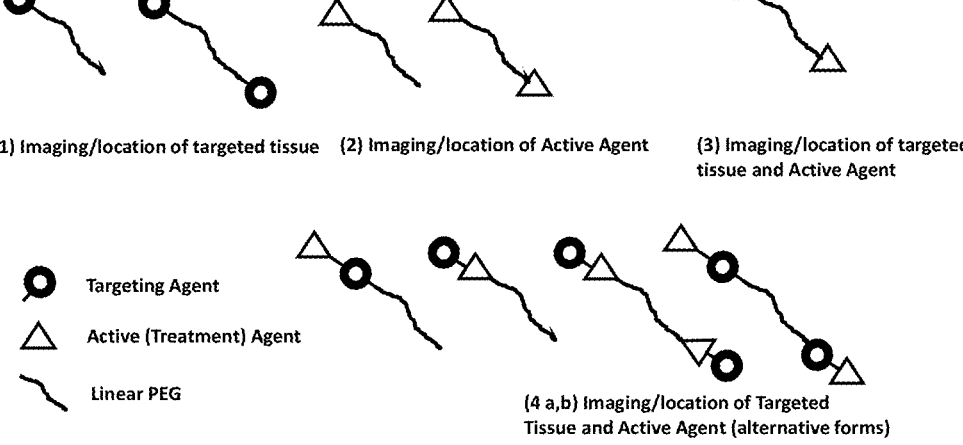
FIG. 1B is a non-limiting formulaic representation of a nanoconstruct (NC) having linear PEG with one or more additives associated thereon. Form (1) depicts a targeting agent (TA) conjugated or associated with the PEG. Form (2) depicts an active agent, such as a therapeutic molecule, conjugated or associated with the PEG. Forms (3) and (4a,b) depict alternative structures of the NC with both the TA and active agent conjugated or associated with the PEG. These representations are not intended to be limiting in the amount or ratio of agents thereon.

As noted above, the nanoconstructs (NCs) include a backbone or platform which may have one or more additives associated thereto. In some instances, the NCs have a plurality of termini to which the additives are associated. The additives present on or in, or (covalently) attached to the NCs may be all the same or may be a combination of different additives. FIG. 1A shows multiple forms of a multi-armed NC having one or more additives thereon. FIG. 1B shows multiple forms of a linear NC having one or more additives thereon.

In some instances, the backbone or platform is selected from a polyethylene glycol (PEG), a polyethyleneimine (PEI), polypropylene glycol, polyvinyl alcohol, polyacrylic acid, polymethacrylic acid, polymethyl methacrylate, polymethylacrylate, polyacrylamide, polymethacrylamide, polylactic acid, polyglycolic acid, polyamidoamine and copolymers thereof. The backbone or platform may be considered symmetrical or unsymmetrical, depending on their structure. These backbones or platforms may be modified, as needed, to include reactive functional groups thereon, such as, but not limited to, amine groups, maleimide groups, N-hydroxy succinimides, sulfonic acids, carboxylates, thiols, alcohols, ketones, esters, alkenes, alkynes, DBCOs, isothiocyanates, acyl halides, alkyl halides, aldehydes, and aromatics. Such reactive functional groups may be used to associate one or more additives to the backbone or platform, such as by covalent association.

In some instances, the nanoconstructs include a backbone or platform that is multi-armed and optionally has one or more additives associated thereto. In some instances, the multi-armed NCs have one or more additives associated thereto and at least one arm of the multi-armed NCs is free of the one or more additives, meaning at least one arm does not include the additive(s) associated to other arms of the multi-armed NC. In some cases, the multi-armed NC has at least one free arm; at least two free arms; at least three free arms; at least four free arms; at least five free arms; at least six free arms; at least seven free arms; at least eight free arms; or at least nine free arms; with the understanding that at least one arm has an additive associated thereto.

In some instances, the one or more additives associated to the multi-armed NC includes at least two additives, such as a targeting agent (TA) and a therapeutic (i.e., a photosensitizer, chemotherapeutic, radiotherapeutic, etc.). In certain such instances, the ratio of the at least two additives can be selected to be from 2 to 1, 3 to 1, 4 to 1 and 5 to 1, depending on the number of arms present on the multi-armed NC.

Methods of synthesizing nanoconstructs having such backbones or platforms are known to the skilled person, as well as methods of chemically modifying the backbones or platforms to include selected reactive functional groups thereon. In some instances, such nanoconstructs may be obtained directly from commercial sources.

a. Polyethylene Glycol (PEG) Backbone or Platform

In some instances, the backbone or platform of each of the nanoconstructs is or includes a linear or multi-armed polyethylene glycol (PEG). In some instances, the nanoconstructs include only multi-armed PEGs. Such multi-armed PEGs can have 2, 3, 4, 5, 6, 7, 8, 9, 10 or more arms. In some instances, a two-armed PEG includes a linker or linking group between the two arms. In some instances, the nanoconstructs include only multi-armed PEGs having same number of arms, such as 8 arms (i.e., 8PEG). The 8PEG can have additional functionality thereon, such as at termini of the arms, where the 8PEG can be an 8PEG amine (8PEGA) or an 8PEG maleimide (8PEGMAL).

In some embodiments, a multi-armed PEG for imaging may be defined as a nanocomposition where individual PEG chains are covalently bound or associated via an intermediate molecular anchor group in the form of PEG1-X-PEG2, where X represents the molecular anchor group. PEG1 and PEG2 may be the same or different PEGs of any suitable length. PEGs of those described, which can be bound together in this form, may individually be branched or linear. In this way two or more linear or branched PEGs may be bound or associated together. Without limitation, the molecular anchor group may be, for example: a block co-polymer, an antibody, a small molecule, a hetero or bi-functional linker, or a peptide.

In some instances of PEG-based backbones or platforms, the number of protons, depending upon the nanoconstructs, can be greater or lesser than 3,600, can be from about 30 to about 30,000, 200 to about 30,000, greater than about 500, greater than about 1500, greater than about 4,000, greater than about 5,000, about 200 to about 10,000, about 3,000 to about 7,000 and all values and sub-ranges contained within these ranges.

In some instances, the multi-armed PEG has one or more additives associated thereto. In some instances, the multi-armed PEG has one or more additives associated thereto and at least one arm of the multi-armed PEG is free of the one or more additives, meaning at least one arm does not include the additive(s) associated to other arms of the multi-armed PEG. In some cases, the multi-armed PEG has at least one free arm; at least two free arms; at least three free arms; at least four free arms; at least five free arms; at least six free arms; at least seven free arms; at least eight free arms; or at least nine free arms; with the understanding that at least one arm has an additive associated thereto.

In some instances, the one or more additives present on the multi-armed NC includes at least two additives, such as a targeting agent (TA) and a therapeutic (i.e., a photosensitizer, chemotherapeutic, radiotherapeutic, etc.). In certain such instances, the ratio of the at least two additives can be selected to be from 2 to 1, 3 to 1, 4 to 1 and 5 to 1, depending on the number of arms present on the multi-armed NC.

In some instances, the nanoconstruct backbone itself is made of or is made primarily of polyethylene glycol (PEG), e.g., at least about 85% PEG, at least 90% PEG, at least 95% PEG, at least 99% PEG, at least 99.9% PEG and up to 100% PEG.

Figure 1C:
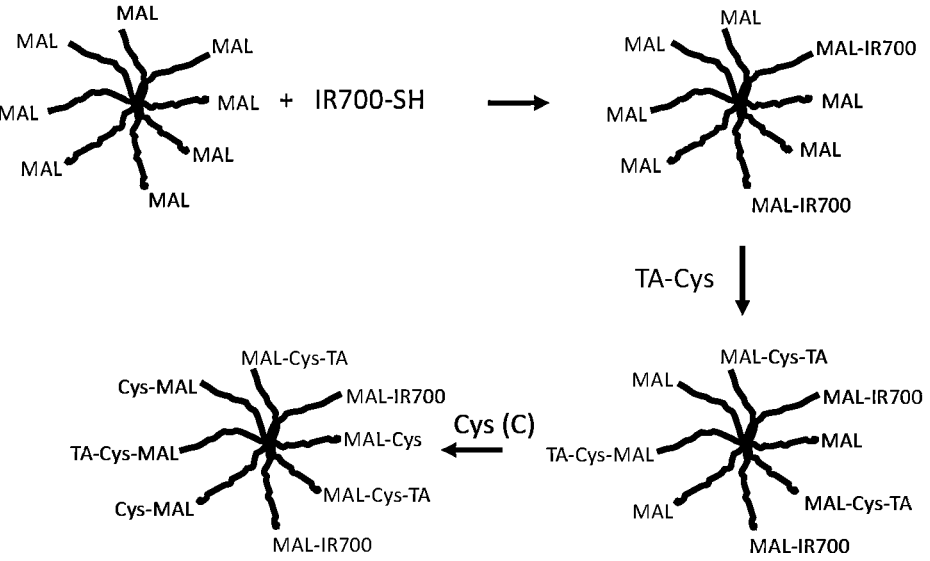
FIG. 1C shows an exemplary flow diagram of a synthetic process for making a nanoconstruct having one or more additives associated thereto.

In one instance, a multi-armed PEG is polyethylene glycol amine, such as 8-arm polyethylene glycol amine (8PEGA), which is a non-limiting example of a biocompatible polymer that allows for a range of modifications. Typically, the amine groups may be used for covalent anchoring of a range of additives. In some other instances, other arms of the polymer may be converted to maleimide groups to provide, for example a multi-armed polyethylene glycol maleimide, such as 8-arm polyethylene glycol maleimide (8PEGMAL), permitting the attachment of various, as an example, cysteine terminated peptides. An exemplary process is shown in FIG. 1C.

In some non-limiting instances, for the PEG-based NCs the intrinsic flexibility of the polyethylene oxide chain and the slow translational diffusion creates an exploitable set of physical and dynamic conditions for selective MR imaging of such PEG protons using 1H NMR. Specifically, PEG's fast chain motions with correlation times of approximately 0.1 ns provide sufficient averaging of the proton dipole-dipole interaction to yield a long nuclear spin transverse relaxation time T2. In contrast to fast internal chain dynamics, the PEG molecule's high molecular weight yields a translational diffusion constant that is two orders of magnitude slower than that of water molecules. Therefore, the water signal can be effectively suppressed by large diffusion gradients so that only the ethylene oxide signal remains due to the combination of its long T2 time and slow diffusion. For instance, the MR signal intensity decays as:

$$M_{xy}(b,TE)=M_{xy}(0)e^{\char`^}(-bD_e-TE/T_2)$$

where the b value is determined by the magnetic field gradient magnitude and duration, D is the translational diffusion constant of either water or PEG, such as 8PEG, TE is the echo time, and T2 is the transverse spin relaxation time. In addition, the symmetry of the ethylene oxide monomer gives rise to a single chemical shift for all four protons and each 40 kDa polymer molecule, when evaluating 8PEG, carries approximately 3,600 protons, creating a large molar amplification of the NMR or MRI signal. By performing a diffusion-weighted, fast spin-echo (FSE) with high b values and long TE times, water signals, due to fast diffusion, and fat signals, due to short T2 times, can be effectively suppressed and the PEG-based NC signal can be selectively imaged. In vivo, a small portion of water signal intensity at high b values will likely remain due to restricted diffusion of water molecules in cells, but these signals can either be removed or distinguished from the PEG-based NC signal due to the −1 ppm difference between water and ethylene glycol protons in traditional $^1$H NMR.

2. Additives

In the methods described, the nanoconstructs can have one or more additives associated thereto. These additives include active agents which may be selected from the group consisting of targeting agents, therapeutic agents, chemotherapeutic agents, radiotherapeutic agents, photosensitizer agents, sonosentizer agents, imaging agents, diagnostic agents, photoacoustic agents, theranostic agents, and combinations thereof.

For the one or more additives associated to the nanoconstructs of the MRI agent, such association to the NC backbone or platform allows for ease of quantification of the additives by imaging of the MRI agent. In other words, knowing the number of additives present on the NCs of the MRI agent and the concentration of NCs in the agent allows for measuring how much of the NCs, as well as how much of the additive, is present in an image of the MRI agent. It also, in some instances, allows for real-time tracking of a treatment whereby the MRI agent administered can be imaged at various times.

In some instances, the one or more additives can be associated with the nanoconstruct's backbone or platform, by way of, without particular limitation: chemical bonds (e.g., covalent, ionic, Van der Waals); sterically or mechanically, such as through steric hinderance or physical capture within or by the backbone or platform. The one or more additives can be a part of the molecular structure that makes up the backbone or platform of the NC; and combinations and variations of aforementioned are also possible. The one or more additives can be added prior to the formation of the nanoconstructs, during the formation of the nanoconstructs, after the formation of the nanoconstructs, as well as combinations and variations of these.

Methods of covalent conjugation of the one or more additives to the backbone are known to the person of ordinary skill in the art. These methods can include, without limitation, click chemistries, reactions between a functional group on the backbone and a functional group on the additive, where these functional groups may include, without limitation alkyl halides, acyl halides, aromatic phenyls, aromatic halides (such as iodo), carboxylic acids, sulfonic acids, phosphoric acids, alcohols (such as primary), maleimides, esters, thiols, azides, aldehydes, alkenes (mono or diene), isocyanates, isothiocyanates, amines, anhydrides, or thiols. Selection of the appropriate reactive functional groups to achieve covalent conjugation and the methods and conditions needed to form the covalent attachment between the backbone or platform and an additive are well-known to the skilled person.

The one or more additives may be known active agents which may include or be modified to include reactive functional groups capable of being coupled to reactive functional groups present on the nanoconstructs, as described above. The person of ordinary skill in the art is familiar with the selection of reactive functional groups which permit such covalent coupling and the synthetic methods to covalently attach active agents to the nanoconstructs.

In some instances, the one or more additives are an active agent selected from methylene blue, chlorin e6 (Ce6), coomassie blue, gold, a tetrapyrrole compound, a cyanine dye, a porphyrin, a chlorin, phthalocyanine (such as IR700 and derivatives thereof), a bacteriochlorin, HPPH, TOOKAD, LUZ 11, BC19porphyrin, a phenothiazinium salt, a benzophenothiazinium salt, a halogenated xanthene, a squaraine, toluidine blue O, PP9004, EtNBS, rose bengal, ASQI, a BODIPY (such as zinc(II) dipicolylamine di-iodoBODIPY or BIMPy-BODIPY), a transition metal co-ordination compound, and combinations thereof.

In some instances, the active agent is a photosensitizer, such as a phthalocyanine. An exemplary phthalocyanine includes IR700 and derivatives thereof. Phthalocyanine dyes, such as IR700 and derivatives thereof, are described in U.S. Published Application No. 2021/0085790 A1 at paragraphs [0074]-[0080] and [0093]-[0113], which are incorporated in relevant part herein. Such photosensitizers, as described in U.S. Publication No. 2021/0085790 A1, may be used as the one or more additives in the nanoconstructs described here.

In some instances, the one or more additives are an active agent which is a transition metal co-ordination compound, and the transition metal co-ordination compound includes a metal selected from the group consisting of ruthenium, rhodium, platinum, gold and iridium, zinc, copper, and palladium.

Additional exemplary additives, which act as active agents, that may form a part of the nanoconstructs and formulations including the nanoconstructs, include, but are not limited to, agents that induce apoptosis; polynucleotides (e.g., anti-sense, ribozymes, siRNA); polypeptides (e.g., enzymes and antibodies (and fragments thereof)); agents that bind (e.g., oligomerize or complex) with a Bcl-2 family protein such as Bax; alkaloids; alkylating agents; antibiotics; antimetabolites; hormones; monoclonal or polyclonal antibodies (e.g., antibodies conjugated with anticancer drugs, toxins, defensins), toxins; radionuclides; biological response modifiers (e.g., interferons (e.g., IFN-a) and interleukins (e.g., IL-2); adoptive immunotherapy agents; hematopoietic growth factors; agents that induce cell differentiation (e.g., all-trans-retinoic acid); gene therapy reagents (e.g., antisense therapy reagents and nucleotides); angiogenesis inhibitors; proteosome inhibitors: NF-KB modulators; anti-CDK compounds; HDAC inhibitors; chemotherapeutic agents (e.g., doxorubicin or cisplatin) and the like. Numerous other examples are known to those skilled in the art.

Examples of sonosensitizer agents include, but are not limited to, porphyrins (e.g., hematoporphyrin, diacetylhematoporphyn-mitomycin-C conjugate, photofrin II, mesoporphyrin, protoporphyrin IX, copper protoporphyrin, tetraphenylporphine tetrasulfonate, ATX-70, ATX-SI0, pheophorbide-a, CIAI-phtalocyanine tetrasulfonate, and chlorine PAD-S31), tenoxicam, piroxicam, rose bengal, erythrosine B, merocyanine 540, dimethylformamide, cytosine arabinoside, pyridoxarbazole, 2,2'-azobis(2-amdinopropane), 5,5'-dimethyl-1-pyrroline-X-oxide, e-pyridyl-1-oxide-N-t-butylnitrone, and anti-cancer agents (e.g., nitrogen mustard, cyclophosmadmide, bleomycin, adriamycin, FAD104, amphotericin B, mitomycin C, daunomycin, cisplatin, etopside, diaziquone, dihydroxy(oxbi-guoanido)boron, and 5-fluorouracil) (See also e.g., Rosenthal et al., Ultrasonics Sonochemistry 11 (2004) 349; herein incorporated by reference in its entirety).

Exemplary active agents that can induce or stimulate apoptosis include, but are not limited to, tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Ber-Ab! kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

Exemplary alkylating agents include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

Exemplary antimetabolites include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

Exemplary chemotherapeutic agents include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide); and 17) gonadotropin-releasing hormone analogs (e.g., leuprolide).

In some instances, imaging agents can be selected from magnetic materials (e.g., iron for MRI); proteins that catalyze luminescent reactions (e.g., luciferins such as luciferase for bioluminescent imaging); fluorescent dyes (e.g., rhodamine or fluorescein isothiocyanate for fluorescent imaging); fluorescent proteins (e.g., green fluorescent protein); and radioactive elements (e.g., for autoradiography).

In some instances, the one or more additives are active agents which are targeting agents which allow the nanoconstructs to target a specific tissue or lumen, when administered to a subject. In some instances, the targeting agent targets cancers or solid tumors.

In some instances, the one or more additives are active agents which are peptides. In some cases, the peptides are cancer targeting peptides without particular limitation, such as selected from the group consisting of an RGD including cRGD, iRGD, and F3; and NGR peptides and iNGR. In some other instances, the peptides are cardiac targeting peptides without particular limitation, such as a peptide selected from SEQ ID NO: 1 to SEQ ID NO: 48. The CTPs of Table 1 are listed below and are further defined as follows. In an embodiment there is a twelve amino acid CTP (CTP12aa) having a sequence of Ala-Pro-Trp-His-Leu-SerSer-Gln-Tyr-Ser-Arg-Thr (SEQ ID NO: 1). In an embodiment there is a six amino acid CTP (CTP6aa) having a sequence of SQYSRT (SEQ ID NO: 5), or a twelve amino acid CTP having a sequence of AA WHLSSQYSRT (SEQ ID NO: 2 (CTP-P2A)) In certain embodiments the sequence of Xaa1 Xaa2 Y Xaa3 Xaa4 T (SEQ ID NO: 4), in which Xaa1, Xaa2, Xaa3, and Xaa4 is any naturally occurring amino acid. In certain embodiments, Xaa1 in the CTP 6aa of SEQ ID NO: 4 is serine (S). In certain embodiments, Xaa2 in the CTP6aa of SEQ ID NO: 4 is glutamine (Q). In certain embodiments, Xaa3 in the CTP6aa of SEQ ID NO: 4 is serine (S). In certain embodiments, Xaa4 in the CTP6aa of SEQ ID NO: 1 is arginine (R). In certain embodiments, Xaa1 and Xaa2 in the CTP6aa of SEQ ID NO: 4 are serine (S) and glutamine (Q), respectively. In certain embodiments, Xaa1 and Xaa3 in the CTP6aa of SEQ ID NO: 4 are both serine (S). In certain embodiments, Xaa1 and Xaa4 in the CTP6aa of SEQ ID NO:4 are serine (S) and arginine (R), respectively. In certain embodiments, Xaa2 and Xaa3 in the CTP6aa of SEQ ID NO:4 are glutamine (Q) and serine (S), respectively. In certain embodiments, the CTP6aa comprises the sequence SQYSRT (SEQ ID NO: 5). The CTPs of Table 1 are further defined as follows. In one aspect the CTP6aa comprises the sequence of S Q Xaa1 S R Xaa2 (SEQ ID NO: 6). In certain embodiments, Xaa1 in the CTP6aa of SEQ ID NO: 6 is alanine (A) and the CTP6aa comprises the sequence of SQASRXaa2 (SEQ ID NO: 7), or optionally, Xaa1 in the CTP6aa of SEQ ID NO: 6 is tryptophan (W) and the CTP6aa comprises the sequence of SQWSRXaa2 (SEQ ID NO: 8), or Xaa1 in the CTP6aa of SEQ ID NO: 6 is tyrosine (Y) and the CTP6aa comprises the sequence of SQYSRXaa2 (SEQ ID NO: 8). In certain embodiments, Xaa2 in the CTP6aa of SEQ ID NO: 6 is threonine (T), and Xaa1 in the CTP6aa of SEQ ID NO: 6 is alanine (A), tryptophan (W), or tyrosine (Y) comprising the sequence of SQASRT (SEQ ID NO: 10), SQWSRT (SEQ ID NO: 11), or SQYSRT (SEQ ID NO: 5), respectively. In certain embodiments, Xaa2 in the CTP6aa of SEQ ID NO: 6 is alanine (A). In certain embodiments, Xaa1 in the CTP6aa of SEQ ID NO: 6 is tyrosine (Y) and Xaa2 is alanine (A). In certain embodiments, the CTP6aa comprises the sequence SQYSRT (SEQ ID NO: 5). The CTPs of Table 1 are further defined as follows. In certain embodiments, Xaa1 in the CTP6aa of SEQ ID NO:4 is serine (S). In certain embodiments, Xaa2 in the CTP6aa of SEQ ID NO: 4 is glutamine (Q). In certain embodiments, Xaa3 in the CTP6aa of SEQ ID NO: 4 is serine (S). In certain embodiments, Xaa4 in the CTP6aa of SEQ ID NO: 4 is arginine (R). In certain embodiments, Xaa1 and Xaa2 in the CTP6aa of SEQ ID NO: 4 are serine (S) and glutamine (Q), respectively. In certain embodiments, Xaa1 and Xaa3 in the CTP6aa of SEQ ID NO: 4 are both serine (S). In certain embodiments, Xaa1 and Xaa4 in the CTP6aa of SEQ ID NO:4 are serine (S) and arginine (R), respectively. In certain embodiments, Xaa2 and Xaa3 in the CTP6aa of SEQ ID NO:4 are glutamine (Q) and serine (S), respectively. In certain embodiments, the CTP6aa comprises the sequence SQYSRT (SEQ ID NO: 5). In certain embodiments, a peptide comprising a CTP6aa comprising the sequence of Xaa1 Xaa2 WXaa3 Xaa4 T (SEQ ID NO: 23), in which Xaa1, Xaa2, Xaa3, and Xaa4 is any naturally occurring amino acid. In certain embodiments, Xaa1 in the CTP6aa of SEQ ID NO:6 is alanine (A) and the CTP6aa comprises the sequence of SQASRXaa2 (SEQ ID NO: 7), or optionally, Xaa1 in the CTP6aa of SEQ ID NO: 6 is tryptophan (W) and the CTP6aa comprises the sequence of SQWSRXaa2 (SEQ ID NO: 8), or Xaa1 in the CTP6aa of SEQ ID NO: 6 is tyrosine (Y) and the CTP6aa comprises the sequence of SQYSRXaa2 (SEQ ID NO: 9). In certain embodiments, Xaa2 in the CTP6aa of SEQ ID NO: 6 is threonine (T), and Xaa1 in the CTP6aa of SEQ ID NO: 6 is alanine (A), tryptophan (W), or tyrosine (Y) comprising the sequence of SQASRT (SEQ ID NO: 10), SQWSRT (SEQ ID NO: 11), or SQYSRT (SEQ ID NO: 5), respectively. In certain embodiments, Xaa2 in the CTP6aa of SEQ ID NO: 6 is alanine (A). In certain embodiments, Xaa1 in the CTP6aa of SEQ ID NO: 6 is tyrosine (Y) and Xaa2 is alanine (A). In certain embodiments, the CTP6aa comprises the sequence SQYSRT (SEQ ID NO: 5). In certain embodiments, a peptide comprising a CTP6aa of SEQ ID NO: 4 and SEQ ID NO: 6, for example SEQ ID NO: 5, is a recombinant or synthetically prepared peptide.

TABLE 1

Cardiac Targeting Peptides for use as Targeting Agents

| ID Number | Sequence |
|---|---|
| (SEQ ID NO: 1) | APWHLSSQYSRT |
| (SEQ ID NO: 2) | AAWHLSSQYSRT (CTP-P2A) |
| (SEQ ID NO: 3) | Amiodarone-SQYSRT (CTP-B) |
| (SEQ ID NO: 4) | Xaa1 Xaa2 Y Xaa3 Xaa4 T |
| (SEQ ID NO: 5) | SQYSRT (CTP-B) |
| (SEQ ID NO: 6) | S Q Xaa1 S R Xaa2 |
| (SEQ ID NO: 7) | SQASRXaa2 |
| (SEQ ID NO: 8) | SQWSRXaa2 |
| (SEQ ID NO: 9) | SQYSRXaa2 |
| (SEQ ID NO: 10) | SQASRT |
| (SEQ ID NO: 11) | SQWSRT |
| (SEQ ID NO: 12) | S Xaa2 Y Xaa3 Xaa 4 T |
| (SEQ ID NO: 13) | Xaa1 Q Y Xaa3 Xaa4 T |
| (SEQ ID NO: 14) | Xaa1 Xaa2 y s Xaa4 T |
| (SEQ ID NO: 15) | Xaa1 Xaa2 Y Xaa3 RT |
| (SEQ ID NO: 16) | SQ Y Xaa3 Xaa4 T |
| (SEQ ID NO: 17) | S Xaa2 Y S Xaa4 T |
| (SEQ ID NO: 18) | S Xaa2 Y Xaa3 R. T |
| (SEQ ID NO: 19) | Xaa1 Q Y S Xaa4 T |
| (SEQ ID NO: 20) | S Xaa2Y S RT |
| (SEQ ID NO: 21) | Xaa1 Q Y SRT |
| (SEQ ID NO: 22) | SQ Y Xaa3 RT |
| (SEQ ID NO: 23) | Xaa1 Xaa2 W Xaa3 Xaa4 T |
| (SEQ ID NO: 24) | APWHLS (CTP-A) |
| (SEQ ID NO: 25) | Amiodarone-AAWHLSSQYSRT (CTP-P2A) |
| (SEQ ID NO: 26) | H4A APW ALSSQYSRT |
| (SEQ ID NO: 27) | L5A APWHASSQYSRT |
| (SEQ ID NO: 28) | S6A APWHLASQYSRT |
| (SEQ ID NO: 29) | S7A APWHLSAQYSRT |
| (SEQ ID NO: 30) | Q8A APWHLSSAYSRT |
| (SEQ ID NO: 31) | Y9A APWHLSSQASRT |
| (SEQ ID NO: 32) | S1OA APWHLSSQYART |
| (SEQ ID NO: 33) | R11A APWHLSSQYSAT |

TABLE 1-continued

Cardiac Targeting Peptides for
use as Targeting Agents

| ID Number | Sequence |
|---|---|
| (SEQ ID NO: 34) | T12A<br>APWHLSSQYSRA |
| (SEQ ID NO: 35) | W3A<br>APAHLSSQYSRT |
| (SEQ ID NO: 36) | APWHLSSQYSRT |
| (SEQ ID NO: 37) | HLSSQYSR |
| (SEQ ID NO: 38) | APWHLSSQYSR |
| (SEQ ID NO: 39) | PWHLSSQYSRT |
| (SEQ ID NO: 40) | PWHLSSQYSR |
| (SEQ ID NO: 41) | APX1HLSSQYSRT where X1 is W or Y |
| (SEQ ID NO: 42) | APWHLSSQX1SRT where X1 is W or Y |
| (SEQ ID NO: 43) | PX1HLSSQYSRT where X1 is W or Y |
| (SEQ ID NO: 44) | PWHLSSQX1SRT where X1 is W or Y |
| (SEQ ID NO: 45) | X1HLSSQYSRT where X1 is W or Y |
| (SEQ ID NO: 46) | WHLSSQX1SRT where X1 is W or Y |
| (SEQ ID NO: 47) | X1HLSSQYSR where X1 is W or Y |
| (SEQ ID NO: 48) | WHLSSQX1SR where X1 is W or Y |

SEQ ID NOS 1-35 are disclosed and taught in WO 2019/226785.
SEQ ID NOS 36-48 are disclosed and taught in U.S. Pat. No.
9,249,184 (and correspond to sequence numbers 1-13 in U.S. Pat.
No. 9,249,184, respectively)

In some instances, the methods described and the one or more additives exclude imaging dyes or agents, and other such materials or compounds that may be viewed as undesirable, especially for use with humans. Such undesirable dyes and agents may be heavy metal based, and use or contain metals, metal oxides, or metal compounds or complexes, such as iron, iron-platinum, magnesium and manganese. Such less-desirable materials or compounds can include gadolinium-based materials. Accordingly, the nanoconstructs can be free or substantially free from heavy metals (such as gadolinium), e.g., the nanoconstruct contains less than about 10 ppm heavy metals, less than about 1 ppm heavy metals, and less than about 0.1 ppm heavy metals, and zero heavy metals. Heavy metals would include titanium and all heavier metals.

For some of the additives described, such as photosensitizers and sonosensitizers, it is understood that these active agents can require the use of activators to activate such agents. Any activator that activates the active agent can be utilized. In general, activators provide a source of energy that results in the active agent, for example, releasing energy (e.g., in the form of free radicals) that leads to cell death or destruction. Exemplary activators include, but are not limited to, light, heat, radiation, sound, and the like. In some instances, activators may be pharmaceutical agents which activate therapeutic agents (e.g., chemotherapeutic agents). For example, verapamil can be used to active or improve efficacy of chemotherapeutic agents (e.g., doxorubicin).

Various activators, activating systems, and methods and conditions for applying these to additives to activate them are known in the art. As an example, an activator can be sound (e.g., sonodynamic therapy). Sonodynamic therapy is based on the synergistic effect of ultrasound and a sonosensitizer. The effect can be localized by focusing the ultrasound on a defined region (e.g., regions of target tissue). The ultrasound can be delivered transdermally to a specific region of target tissue. In sonodynamic therapy an ultrasound dependent enhancement of cytotoxic activities of certain compounds (sonosensitizers) can be based on applying ultrasound, which is a mechanical wave with periodic vibrations of particles in a continuous, elastic medium at frequencies equal to or greater than 20 kHz. In liquids, its velocity of about 1000-1600 m/s, which translates into the wavelength range from micrometers to centimeters. In some cases, sound is generated outside of the body and targeted through tissue to the desired treatment region where nanoconstructs having sonosensitizers are present.

In some instances of the methods described, the above additives described may be co-administered during the method without being associated to the nanoconstructs. Methods for administration of such additives to a subject are known to the skilled person.

EXAMPLES

Example 1: Fast Spin-Echo (FSE) Imaging of PEG
Nanoconstructs

Materials and Methods 7.5 mm NMR tubes were prepared with 40 kDa 8PEG (JenKem, Inc.) of varying concentrations (0, 0.05, 0.1, 0.5, 1.0, 3.0, and 5.0 mg/mL) surrounded by agarose gel (Sigma).

Selective spin-echo images and selective fast spin-echo images of the PEG of different concentrations were obtained (not shown) using 7T animal imaging system manufactured by Varian. The images showed much higher noise in the spin-echo image as compared to the fast spin-echo images. Both the conventional diffusion-weighted spin echo and diffusion-weighted fast-spin-echo NMR images of the PEG protons were acquired in a total imaging time of 6 minutes.

Results and Discussion

Figure 2:
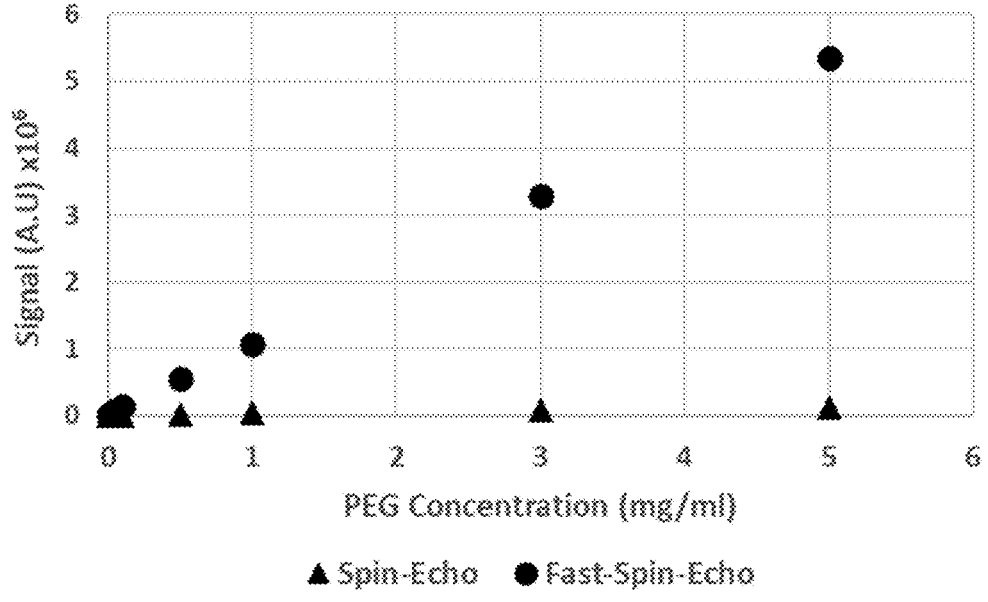
FIG. 2 shows a graph of the 1H NMR signal vs. PEG concentration of a fast spin-echo image and a conventional spin-echo image. As depicted in FIG. 2, the signal of the fast spin-echo image was 30 times greater than the signal detected using a conventional spin-echo technique.

Diffusion filtered, T2 filtered fast-spin echo imaging of 8PEG allowed for single-shot k-space sampling of the PEG proton signal. Signal averaging for 6 minutes yielded a PEG proton image with signal 30 times larger than that of the conventional spin-echo imaging (see FIG. 2). Imaging of PEG concentrations using fast spin-echo at concentrations as low as 0.05 mg/ml was possible.

Example 2: Measurement of T2 and Translational
Diffusion Coefficients (TDCs) of PEGs Materials and Methods Samples were prepared by adding the described PEGs (see Table 2 below) into separate tubes and dissolving in 99.9% D20. More specifically, the samples were prepared at a concentration of 10 mg/per mL dissolved in deuterium oxide (D20) and scanned on a 700 MHz Varian/Agilent high resolution NMR spectrometer at 25° C.

Diffusion was estimated with a convection-compensated, stimulated-echo NMR pulse sequence as part of the Varian DOSY toolbox. Diffusion delay times of D=100 ms and d=2 ms were used with magnetic field gradients sufficient to create b=59,320 s/mm2. Specifically, twenty-one b values of 8.98, 2972, 5935, 8902, 11865, 14830, 17794, 20757, 23728, 26690, 29657, 32619, 35594, 38551, 41519, 44487, 47443, 50410, 53380, 56347, and 59320 s/mm2 were used. The diffusion decay data was fitted to an exponential function in Matlab R200b using the Curve Fitting Toolbox and the translational diffusion coefficient (TDC) was estimated.

T2 values were estimated by using the Varian provided CPMGT2 pulse sequence to acquire the data as a function of TE times. The repetition time of the experiment was 10 seconds and TE times varied between 37.5 ms and 9.6 seconds. Four transients were acquired and averaged. The data were analyzed on the Varian scanner using an exponential decay model and a Levenberg-Marquardt non-linear least squares algorithm to provide an estimation of the T2 values.

T1 values were estimated by using the Varian provided INVREC (inversion recovery) pulse sequence to acquire the data as a function of the inversion recovery time. The repetition time of the experiment was acquired with a repetition time of 10s and inversion recovery times between 62 ms and 8 s. Data were fitted to an inversion recovery model using Levenberg-Marquardt non-linear least squares algorithm on the Varian scanner and T1 times estimated.

Results

The T2 and TDC values of the various PEGs evaluated are given in Table 2 below:

TABLE 2

Results of Analysis of T1, T2, and TDC Values for Various PEGs

| PEG Mwt | | Translational Diffusion Coefficient | T1 | | T2 | |
|---|---|---|---|---|---|---|
| (Da) | Type | (10E−11 m^2/s) | ms | +/− | ms | +/− |
| 3,350 | Linear | 9.81 | 755 | 8 | 593 | 2 |
| 10,000 | Linear | 5.55 | 821 | | 607 | |
| 40,000 | Linear | 2.42 | 811 | | 604 | |
| 20,000 | Star | 4.53 | 845 | | 588 | |
| 40,000 | Star | 3.19 | 791 | | 586 | |

Example 3: Suppression of Fat Signals in the DWFSE of PEG in Phantoms

Materials and Methods

Figure 4A:
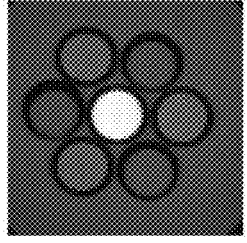
FIG. 4A shows nuclear magnetic resonance imaging of water with a high intensity signal in the center vial due to doping with manganese (Mn) which provides tissue T2 values.
Figure 4B:
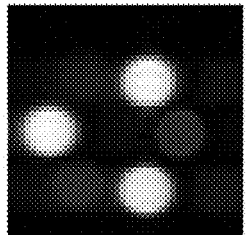
FIG. 4B shows nuclear magnetic resonance imaging using fast spin-echo selective imaging of PEG without application of fat suppression, where the center vial consists of water and the vials at 1:00, 5:00 and 9:00 contain fat while those at 3:00, 7:00, and 11:00 contain PEG dissolved in water (10 mg/mL, 4 mg/mL, and 2 mg/mL, respectively).
Figure 4C:
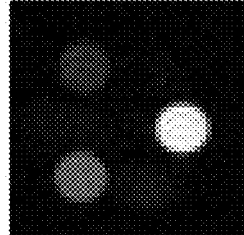
FIG. 4C shows nuclear magnetic resonance imaging using fast spin-echo selective imaging of PEG with the application of fat suppression, where the center vial consists of water and the vials at 1:00, 5:00 and 9:00 contain fat while those at 3:00, 7:00, and 11:00 contain PEG dissolved in water (10 mg/mL, 4 mg/mL, and 2 mg/mL, respectively).

A series of materials with MRI properties mimicking those found in vivo (i.e., an imaging phantom) was prepared consisting of water in a center vial and in surrounding vials, fat in vials at 1:00, 5:00 and 9:00, and PEG dissolved in water at 3:00, 7:00 and 11:00 are shown in FIGS. 4A-4C. A conventional water image is shown in FIG. 4C, which shows high signal intensity in the center vial as it was doped with Mn to provide tissue T2 values.

In a mouse study, Matrigel implants containing 100 microliters of Matrigel each with 10 mg/ml PEG (in one implant) and with 2 mg/ml PEG (in the other implant) was placed at two flank locations on a single mouse weighing 25.4 grams. Standard water proton fast spin echo MRI scans were performed with TR=2000 ms and TE=10 ms to visualize the Matrigel implants.

Results and Discussion

The image of FIG. 4B shows the selective PEG imaging method without fat suppression. The fat signal in this phantom comes from peanut oil, which has been shown to have properties similar to adipose tissue in vivo. It is shown that the fat signal dominates the PEG image.

The image of FIG. 4C shows selective PEG imaging with application of a tuned fat suppression signal. The intensity and frequency of the RF pulse was tuned to provide fat saturation, revealing clean PEG signals that scale with concentrations of 2, 4, and 10 mg/ml.

In vivo, the signal from adipose tissue, i.e. the fat signal, is not sufficiently suppressed by the current PEG imaging protocol(s) and shines through creating an image that is a superposition of PEG and fat protons.

Regarding the mouse study, water images and fat-suppressed PEG images were acquired (images not shown). The combination of b value=5000 s/mm2, and fat suppression also permitted selective PEG imaging. MRI images taken without such b values and TE times will show a conventional water proton image. Adding b-values=5000 s/mm2 and TE=245 ms effectively suppresses the water signal but does not sufficiently suppress long-T2 fat signals, creating an image that is a superposition of PEG and fat signals. Adding fat suppression in combination with high b values and long TE times sufficiently reduces both water and fat signal to create a PEG selective image.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific instances of the invention described herein. Such equivalents are intended to be encompassed by the following claims.

SEQUENCE LISTING

```
Sequence total quantity: 48
SEQ ID NO: 1              moltype = AA  length = 12
FEATURE                   Location/Qualifiers
source                    1..12
                          mol_type = protein
                          organism = synthetic construct
SEQUENCE: 1
APWHLSSQYS RT                                              12

SEQ ID NO: 2              moltype = AA  length = 12
FEATURE                   Location/Qualifiers
source                    1..12
```

-continued

```
                           mol_type = protein
                           organism = Synthetic construct
SEQUENCE: 2
AAWHLSSQYS RT                                                        12

SEQ ID NO: 3              moltype = AA   length = 6
FEATURE                  Location/Qualifiers
source                   1..6
                         mol_type = protein
                         organism = Synthetic construct
MOD_RES                  1
                         note = amiodarone
SEQUENCE: 3
SQYSRT                                                               6

SEQ ID NO: 4             moltype =   length =
SEQUENCE: 4
000

SEQ ID NO: 5             moltype = AA   length = 6
FEATURE                  Location/Qualifiers
source                   1..6
                         mol_type = protein
                         organism = Synthetic construct
SEQUENCE: 5
SQYSRT                                                               6

SEQ ID NO: 6             moltype = AA   length = 6
FEATURE                  Location/Qualifiers
source                   1..6
                         mol_type = protein
                         organism = Synthetic construct
SEQUENCE: 6
SQXSRX                                                               6

SEQ ID NO: 7             moltype = AA   length = 6
FEATURE                  Location/Qualifiers
source                   1..6
                         mol_type = protein
                         organism = Synthetic construct
SEQUENCE: 7
SQASRX                                                               6

SEQ ID NO: 8             moltype = AA   length = 6
FEATURE                  Location/Qualifiers
source                   1..6
                         mol_type = protein
                         organism = Synthetic construct
SEQUENCE: 8
SQWSRX                                                               6

SEQ ID NO: 9             moltype = AA   length = 6
FEATURE                  Location/Qualifiers
source                   1..6
                         mol_type = protein
                         organism = Synthetic construct
SEQUENCE: 9
SQYSRX                                                               6

SEQ ID NO: 10            moltype = AA   length = 6
FEATURE                  Location/Qualifiers
source                   1..6
                         mol_type = protein
                         organism = Synthetic construct
SEQUENCE: 10
SQASRT                                                               6

SEQ ID NO: 11            moltype = AA   length = 6
FEATURE                  Location/Qualifiers
source                   1..6
                         mol_type = protein
                         organism = Synthetic construct
SEQUENCE: 11
SQWSRT                                                               6

SEQ ID NO: 12            moltype =   length =
SEQUENCE: 12
000
```

-continued

```
SEQ ID NO: 13           moltype =   length =
SEQUENCE: 13
000

SEQ ID NO: 14           moltype =   length =
SEQUENCE: 14
000

SEQ ID NO: 15           moltype =   length =
SEQUENCE: 15
000

SEQ ID NO: 16           moltype = AA  length = 6
FEATURE                 Location/Qualifiers
source                  1..6
                        mol_type = protein
                        organism = Synthetic construct
SEQUENCE: 16
SQYXXT                                                              6

SEQ ID NO: 17           moltype = AA  length = 6
FEATURE                 Location/Qualifiers
source                  1..6
                        mol_type = protein
                        organism = Synthetic construct
SEQUENCE: 17
SXYSXT                                                              6

SEQ ID NO: 18           moltype = AA  length = 6
FEATURE                 Location/Qualifiers
source                  1..6
                        mol_type = protein
                        organism = Synthetic construct
SEQUENCE: 18
SXYXRT                                                              6

SEQ ID NO: 19           moltype = AA  length = 6
FEATURE                 Location/Qualifiers
source                  1..6
                        mol_type = protein
                        organism = Synthetic construct
SEQUENCE: 19
XQYSXT                                                              6

SEQ ID NO: 20           moltype = AA  length = 6
FEATURE                 Location/Qualifiers
source                  1..6
                        mol_type = protein
                        organism = Synthetic construct
SEQUENCE: 20
SXYSRT                                                              6

SEQ ID NO: 21           moltype = AA  length = 6
FEATURE                 Location/Qualifiers
source                  1..6
                        mol_type = protein
                        organism = Synthetic construct
SEQUENCE: 21
XQYSRT                                                              6

SEQ ID NO: 22           moltype = AA  length = 6
FEATURE                 Location/Qualifiers
source                  1..6
                        mol_type = protein
                        organism = Synthetic construct
SEQUENCE: 22
SQYXRT                                                              6

SEQ ID NO: 23           moltype =   length =
SEQUENCE: 23
000

SEQ ID NO: 24           moltype = AA  length = 6
FEATURE                 Location/Qualifiers
source                  1..6
                        mol_type = protein
                        organism = Synthetic construct
SEQUENCE: 24
APWHLS                                                              6
```

-continued

```
SEQ ID NO: 25          moltype = AA   length = 12
FEATURE                Location/Qualifiers
source                 1..12
                       mol_type = protein
                       organism = Synthetic construct
MOD_RES                1
                       note = amiodarone
SEQUENCE: 25
AAWHLSSQYS RT                                                    12

SEQ ID NO: 26          moltype = AA   length = 12
FEATURE                Location/Qualifiers
source                 1..12
                       mol_type = protein
                       organism = Synthetic construct
SEQUENCE: 26
APWALSSQYS RT                                                    12

SEQ ID NO: 27          moltype = AA   length = 12
FEATURE                Location/Qualifiers
source                 1..12
                       mol_type = protein
                       organism = Synthetic construct
SEQUENCE: 27
APWHASSQYS RT                                                    12

SEQ ID NO: 28          moltype = AA   length = 12
FEATURE                Location/Qualifiers
source                 1..12
                       mol_type = protein
                       organism = Synthetic construct
SEQUENCE: 28
APWHLASQYS RT                                                    12

SEQ ID NO: 29          moltype = AA   length = 12
FEATURE                Location/Qualifiers
source                 1..12
                       mol_type = protein
                       organism = Synthetic construct
SEQUENCE: 29
APWHLSAQYS RT                                                    12

SEQ ID NO: 30          moltype = AA   length = 12
FEATURE                Location/Qualifiers
source                 1..12
                       mol_type = protein
                       organism = Synthetic construct
SEQUENCE: 30
APWHLSSAYS RT                                                    12

SEQ ID NO: 31          moltype = AA   length = 12
FEATURE                Location/Qualifiers
source                 1..12
                       mol_type = protein
                       organism = Synthetic construct
SEQUENCE: 31
APWHLSSQAS RT                                                    12

SEQ ID NO: 32          moltype = AA   length = 12
FEATURE                Location/Qualifiers
source                 1..12
                       mol_type = protein
                       organism = Synthetic construct
SEQUENCE: 32
APWHLSSQYA RT                                                    12

SEQ ID NO: 33          moltype = AA   length = 12
FEATURE                Location/Qualifiers
source                 1..12
                       mol_type = protein
                       organism = Synthetic construct
SEQUENCE: 33
APWHLSSQYS AT                                                    12

SEQ ID NO: 34          moltype = AA   length = 12
FEATURE                Location/Qualifiers
source                 1..12
                       mol_type = protein
```

```
                          organism = Synthetic construct
SEQUENCE: 34
APWHLSSQYS RA                                                          12

SEQ ID NO: 35            moltype = AA  length = 12
FEATURE                  Location/Qualifiers
source                   1..12
                         mol_type = protein
                         organism = Synthetic construct
SEQUENCE: 35
APAHLSSQYS RT                                                          12

SEQ ID NO: 36            moltype = AA  length = 12
FEATURE                  Location/Qualifiers
source                   1..12
                         mol_type = protein
                         organism = Synthetic construct
SEQUENCE: 36
APWHLSSQYS RT                                                          12

SEQ ID NO: 37            moltype = AA  length = 8
FEATURE                  Location/Qualifiers
source                   1..8
                         mol_type = protein
                         organism = Synthetic construct
SEQUENCE: 37
HLSSQYSR                                                               8

SEQ ID NO: 38            moltype = AA  length = 11
FEATURE                  Location/Qualifiers
source                   1..11
                         mol_type = protein
                         organism = Synthetic construct
SEQUENCE: 38
APWHLSSQYS R                                                           11

SEQ ID NO: 39            moltype = AA  length = 11
FEATURE                  Location/Qualifiers
source                   1..11
                         mol_type = protein
                         organism = Synthetic construct
SEQUENCE: 39
PWHLSSQYSR T                                                           11

SEQ ID NO: 40            moltype = AA  length = 10
FEATURE                  Location/Qualifiers
source                   1..10
                         mol_type = protein
                         organism = Synthetic construct
SEQUENCE: 40
PWHLSSQYSR                                                             10

SEQ ID NO: 41            moltype = AA  length = 12
FEATURE                  Location/Qualifiers
source                   1..12
                         mol_type = protein
                         organism = Synthetic construct
UNSURE                   3
                         note = W or Y
SEQUENCE: 41
APXHLSSQYS RT                                                          12

SEQ ID NO: 42            moltype = AA  length = 12
FEATURE                  Location/Qualifiers
source                   1..12
                         mol_type = protein
                         organism = Synthetic construct
UNSURE                   9
                         note = W or Y
SEQUENCE: 42
APWHLSSQXS RT                                                          12

SEQ ID NO: 43            moltype = AA  length = 11
FEATURE                  Location/Qualifiers
source                   1..11
                         mol_type = protein
                         organism = Synthetic construct
UNSURE                   2
                         note = W or Y
```

-continued

```
SEQUENCE: 43
PXHLSSQYSR T                                                          11

SEQ ID NO: 44          moltype = AA   length = 11
FEATURE                Location/Qualifiers
source                 1..11
                       mol_type = protein
                       organism = Synthetic construct
UNSURE                 8
                       note = W or Y
SEQUENCE: 44
PWHLSSQXSR T                                                          11

SEQ ID NO: 45          moltype = AA   length = 10
FEATURE                Location/Qualifiers
source                 1..10
                       mol_type = protein
                       organism = Synthetic construct
UNSURE                 1
                       note = W or Y
SEQUENCE: 45
XHLSSQYSRT                                                            10

SEQ ID NO: 46          moltype = AA   length = 10
FEATURE                Location/Qualifiers
source                 1..10
                       mol_type = protein
                       organism = Synthetic construct
UNSURE                 7
                       note = W or Y
SEQUENCE: 46
WHLSSQXSRT                                                            10

SEQ ID NO: 47          moltype = AA   length = 9
FEATURE                Location/Qualifiers
source                 1..9
                       mol_type = protein
                       organism = Synthetic construct
UNSURE                 1
                       note = W or Y
SEQUENCE: 47
XHLSSQYSR                                                             9

SEQ ID NO: 48          moltype = AA   length = 9
FEATURE                Location/Qualifiers
source                 1..9
                       mol_type = protein
                       organism = Synthetic construct
UNSURE                 7
                       note = W or Y
SEQUENCE: 48
WHLSSQXSR                                                             9
```

We claim:

1. A method of imaging a magnetic resonance imaging (MRI) agent, the method comprising:
   (a) administering the MRI agent to a subject, wherein the MRI agent comprises nanoconstructs each having a plurality of equivalent protons and an average molecular weight in a range of about 300 Da to about 300 kDa, and the nanoconstructs each have a T2 relaxation time greater than at least about 250 ms;
   (b) using an MRI device to obtain a nuclear magnetic resonance scan of the that selectively images the nanoconstructs, wherein (b) comprises:
      (i) scanning the subject with the MRI device, using a signal acquisition bandwidth ranging from at least about 2 kHz to about 200 KHz and greater than 8 spin echoes, so that signals from both (A) the plurality of equivalent nanoconstruct protons and (B) water protons are obtained; and
      (ii) applying diffusion filtering to suppress the water proton signals from the scan,
so that the nuclear magnetic resonance scan that selectively images the nanoconstructs is obtained.

2. The method of claim 1, wherein the nanoconstructs each have a translational diffusion coefficient of less than about $2\times10^{-10}$ m$^2$ s$^{-1}$.

3. The method of claim 1, wherein (iii) comprises obtaining at least 3 gradient echoes.

4. The method of claim 1, wherein each of the nanoconstructs has an average molecular weight in a range of about 3 kDa to about 300 kDa.

5. The method of claim 1, wherein the T2 relaxation time is from about 550 ms to about 900 ms.

6. The method of claim 1, wherein the signal acquisition bandwidth is about 2 to about 50 KHz or about 5 to about 100 KHz.

7. The method of claim 1, wherein at least 16 spin echoes are obtained during (b).

8. The method of claim 1, wherein the plurality of equivalent protons comprises about 30 to 27,000 protons, 200 to about 15,000 protons, or about 200 to about 10,000 protons.

9. The method of claim 1, wherein each of the nanoconstructs comprises a linear or multi-armed polyethylene glycol (PEG).

10. The method of claim 9, wherein each of the nanoconstructs comprises one or more additives associated to the multi-armed PEG.

11. The method of claim 10, wherein the one or more additives comprise an active agent selected from the group consisting of targeting agents, therapeutic agents, chemotherapeutic agents, photosensitizer agents, sonosentizer agents, imaging agents, diagnostic agents, photoacoustic agents, theranostic agents, and combinations thereof.

12. The method of claim 10, wherein the one or more additives comprises an active agent selected from the group consisting of methylene blue, chlorin e6 (Ce6), coomassie blue, gold, a tetrapyrrole compound, a cyanine dye, a porphyrin, a chlorin, phthalocyanine, IR700 and derivatives thereof, a bacteriochlorin, HPPH, TOOKAD, LUZ 11, BC19porphyrin, a phenothiazinium salt, a benzophenothiazinium salt, a halogenated xanthene, a squaraine, toluidine blue O, pp 9004, EtNBS, rose bengal, ASQI, a BODIPY (such as zinc(II) dipicolylamine di-iodoBODIPY or BIMPy-BODIPY), a transition metal co-ordination compound, and combinations thereof.

13. The method of claim 10, wherein the one or more additives comprises a targeting agent optionally wherein the targeting agent is a cancer targeting agent; optionally wherein the cancer targeting agent is selected from the group consisting of an RGD including cRGD, IRGD, and F3; and NGR peptides and INGR.

14. The method of claim 10, wherein the one or more additives comprises a targeting agent optionally wherein the targeting agent is a cardiac targeting agent; optionally wherein the cardiac targeting agent is selected from the group consisting of SEQ ID NO: 1 to SEQ ID NO: 48.

15. The method of claim 10, wherein the one or more additives comprises a photosensitizer agent which is phthalocyanine dye, optionally wherein the phthalocyanine dye is IR700.

16. The method of claim 9, wherein at least one arm of the multi-armed PEG is free of the one or more additives.

17. The method of claim 1, wherein each of the nanoconstructs has an average diameter of less than about 50 nm.

18. The method of claim 10, wherein the one or more additives comprises a targeting agent which is a tumor targeting agent; and wherein the method further comprises, following (b):

(c) providing data identifying the shape, structure, and/or position of a tumor in the subject.

19. The method of claim 10, comprising:

(c), following (b), providing data on the concentration of the nanoconstructs and the one or more additives associated to the multi-armed PEG in the subject.

20. The method of claim 1, wherein (b) comprises applying one or more fat saturation techniques.

\* \* \* \* \*